United States Patent [19]

Menichincheri et al.

[11] Patent Number: 5,912,263
[45] Date of Patent: *Jun. 15, 1999

[54] TAXANE DERIVATIVES

[75] Inventors: Maria Menichincheri, Milan; Walter Ceccarelli; Marina Ciomei, both of Corsico; Domenico Fusar Bassini, Montodine; Nicola Mongelli; Ermes Vanotti, both of Milan, all of Italy

[73] Assignee: Pharmacia S.p.A., Milan, Italy

[ * ] Notice: This patent is subject to a terminal disclaimer.

[21] Appl. No.: 08/964,889

[22] Filed: Nov. 5, 1997

Related U.S. Application Data

[63] Continuation of application No. 08/663,080, filed as application No. PCT/EP95/04302, Nov. 2, 1995, Pat. No. 5,719,177.

[30] Foreign Application Priority Data

Nov. 4, 1994 [GB] United Kingdom .................. 9422245
Jun. 7, 1995 [GB] United Kingdom .................. 9511475
Oct. 16, 1995 [GB] United Kingdom .................. 9521168

[51] Int. Cl.$^6$ ................ A61K 31/335; C07D 305/14
[52] U.S. Cl. ..................... 514/449; 549/510; 549/511
[58] Field of Search .................... 549/510, 511; 514/449

[56] References Cited

U.S. PATENT DOCUMENTS 5,719,177   2/1998   Menichincheri et al. ............ 514/449

*Primary Examiner*—Ba K. Trinh
*Attorney, Agent, or Firm*—Oblon, Spivak, McClelland, Maier & Neustadt, P.C.

[57] ABSTRACT

Taxane derivatives modified at 13-position of the taxane derivative skeleton (taxol numbering) of formula (I), wherein R, $R_a$, $R_b$, $R_c$, $R_1$, $R_2$, $R_3$ are appropriate organic residues can be antitumor agents.

22 Claims, No Drawings

TAXANE DERIVATIVES

This is a Continuation of application Ser. No. 08/663,080 filed on Jun. 25, 1996, now U.S. Pat. No. 5,719,177, which was filed as International Application No. PCT/EP95/04302, filed Nov. 2, 1995.

The present invention is directed to new taxane derivatives endowed with antitumour activity, to a process for their preparation and to pharmaceutical compositions containing them.

The taxane family of diterpenes includes Paclitaxel (also named taxol in several publications), isolated and characterized from an extract of bark of *Taxus brevifolia* L., and Cephalomannine (see J.Chem.Soc. Chem. Comm.102, 1979); other taxane analogues are also known and were prepared by semisynthesis starting from 10-deacetyl baccatin III, extracted from the needles of *Taxus baccata* L. (see Wani et al., J.Am.Chem.Soc.93, 2325, 1971; Lovelle et al., Proc.Am.Assoc.Cancer Res.31, 417, 1990). Particularly, paclitaxel is a very potent anticancer drug and is already applied with success to the treatment of platinum-resistant ovarian cancer. Nevertheless there is a continuous need for more potent compounds having the broadest possible spectrum of activity on different cancer types.

The present invention provides taxane derivatives modified at the 13-position of the taxane skeleton (taxol numbering). More especially, the invention provides taxane derivatives of the formula I:

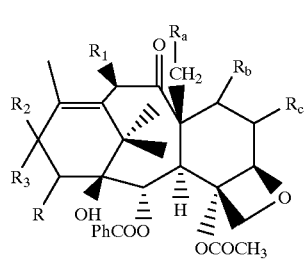

wherein: R represents a hydrogen atom or a hydroxy group, or taken together with $R_3$, a bond;

(i) $R_a$ and $R_c$ are hydrogens and $R_b$ is hydroxy, or (ii) $R_a$ and $R_b$ taken together form a bond and $R_c$ is hydrogen, or (iii) $R_a$ is hydrogen atom and $R_b$ and $R_c$ taken together form a bond, or $R_b$ is azido or amino group and $R_c$ is hydrogen atom;

R1 represents a hydrogen atom, a hydroxy group or a residue of formula —OCOR', —OR', —OSO$_2$R', —OCONR'R", —OCONHR' or —OCOOR' wherein R' and R" are each independently $C_1$–$C_6$ alkyl, preferably methyl, phenyl-$C_2$–$C_6$ alkenyl or phenyl-$C_2$–$C_6$ alkyl, $C_3$–$C_6$ cycloalkyl, $C_2$–$C_6$ alkynyl or a phenyl group, optionally substituted with one, two or three substituents which may be the same or different and which are selected from a halogen atom and $C_1$–$C_6$ alkyl, $C_1$–$C_6$ alkoxy and —CF$_3$ groups; and either (i) $R_2$ and $R_3$ together represent a group of the formula A—N=, as pure E or pure Z isomers or as a mixture of both E and Z isomers, wherein A represents:
a hydrogen atom or a hydroxy, methoxy, acetoxy, amino, methylamino or dimethylamino group, or
d group of the formula Y—NH— wherein Y represents either (a) residue of an amino acid, preferably glycine, phenylglycine, serine, 3-phenylserine, β-alanine and the like, optionally protected at the amino group as a N-benzoyl derivative or as a carbamate, or (b) a chain of the formula II:

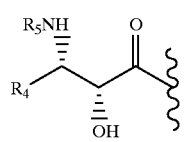

wherein:
$R_4$ is a $C_1$–$C_6$ alkyl, $C_2$–$C_6$ alkenyl, $C_3$–$C_6$ cycloalkyl group or a phenyl or heteroaryl group, optionally substituted with one, two or three substituents which may be the same or different and which are selected from a halogen atom and $C_1$–$C_6$ alkyl, $C_1$–$C_6$ alkoxy, or —CF$_3$ groups; and $R_5$ is —COOR''' or —COR''', or CONHR''' wherein R''' is $C_1$–$C_6$ alkyl, preferably tert-butyl or n-pentyl, $C_2$–$C_6$ alkenyl, preferably 1-methyl-1-propenyl, $C_3$–$C_6$ cycloalkyl, $C_2$–$C_6$ alkynyl or a phenyl group, optionally substituted with one, two or three substituents which may be the same or different and which are selected from a halogen atom and $C_1$–$C_6$ alkyl, $C_1$–$C_6$ alkoxy and —CF$_3$ groups; or
a group of the formula Y or Y—O— wherein Y is as defined above;
a group of the formula COR' wherein R' is as defined above; or (ii) $R_2$ represents a group of the formula B—NH— wherein B represents
a) hydrogen atom,
b) hydroxy group,
c) amino group,
d) a group of the formula Y—(NH)$_n$— wherein Y is as defined above and n is 0 or 1, or
e) a group of the formula Y—O— wherein Y is as defined above;
f) a group of the formula COR' wherein R' is as defined above; and $R_3$ represents hydrogen, or, taken with R, a bond;

and pharmaceutically acceptable salts thereof.

The $R_2$ substituent may be in the R or S configuration. Alternatively the $R_2$ substituent may be in both the R and S configurations i.e. a mixture of stereoisomers is present.

A $C_1$–$C_6$ alkyl group is a straight or branched alkyl group, preferably a $C_1$–$C_4$ alkyl group such as methyl, ethyl, n-propyl, isopropyl, n-butyl, isobutyl, sec-butyl, tert-butyl or n-pentyl. A $C_2$–$C_6$ alkenyl group is a straight or branched alkenyl group, preferably a $C_2$–$C_5$ alkenyl group such as vinyl, allyl, crotyl, 2-methyl-1-propenyl, 1-methyl-1-propenyl, butenyl or pentenyl. A $C_3$–$C_6$ cycloalkyl group is a saturated carbocyclic group of 3 to 6 carbon atoms, such as cyclopropyl, cyclobutyl, cyclopentyl or cyclohexyl.

A halogen is preferably fluorine, chlorine, bromine or iodine.

The heteroaryl group is preferably a 3- to 6-membered, saturated or unsaturated heterocyclyl ring which contains at least one, for example 1, 2 or 3, heteroatoms selected from O, S and N and which is optionally fused to a second 5- or 6-membered, saturated or unsaturated heterocyclyl group containing 1 or more, for example, 1, 2, or 3 hetereoatoms or to a cycloalkyl group or to an aryl group. The 3- to 6-membered heterocycyl ring may be a 3-, 4-, 5- or 6-membered such ring. A cycloalkyl group is generally a said $C_3$–$C_6$ cycloalkyl group. An aryl group is generally phenyl or naphthyl.

Examples of heterocyclyl groups are pyrrolyl, pyrazolyl, imidazolyl, triazolyl, tetrazolyl, oxazolyl, isoxazolyl, thiazolyl, isothiazolyl, thiadiazolyl, thienyl, furyl, aziridinyl, oxiranyl, azetidinyl, pyridinyl, pyrazinyl, pyrimidinyl, pyranyl, pyridazinyl, benzothienyl, benzothiazolyl, benzoxazolyl, isobenzofuranyl, benzofuranyl, chromenyl, indolyl, indolizinyl, isoindolyl, cinnolinyl, indazolyl and purinyl.

A $C_2$–$C_6$ alkenediyl chain can be a straight or branched alkenediyl preferably a $C_2$–$C_4$ alkenediyl chain such as —CH=CH—, —CH=CH—$CH_2$— or —CH($CH_3$)—CH=CH—. The $C_2$–$C_6$ alkynyl group is a straight or branched alkynyl group preferably a $C_2$–$C_4$ alkynyl chain such as ethynyl, propargyl, 1-propynyl, 1-butynyl or 2-butynyl. A $C_1$–$C_6$ alkoxy group can be a straight chain or branched alkoxy group, preferably a $C_1$–$C_4$ alkoxy group such as methoxy, ethoxy, n-propoxy, n-butoxy or tert-butoxy.

Preferred compounds of the invention are taxane derivatives of formula I, wherein:

$R_a$ and $R_c$ are hydrogen atoms and $R_b$ is hydroxy, $R_1$ represents a hydrogen atom, a hydroxy group or a residue of formula —OCOR', —OR', —$OSO_2$R', —OCONR'R", —OCONHR' or —OCOOR' wherein R' and R" are each independently $C_1$–$C_4$ alkyl, $C_2$–$C_5$ alkenyl, $C_3$–$C_6$ cycloalkyl, $C_2$–$C_5$ alkynyl or a phenyl group, optionally substituted with one, two or three substituents which may be the same or different and which are selected from a halogen atom and $C_1$–$C_4$ alkyl, $C_1$–$C_4$ alkoxy and —$CF_3$ groups; and either:

(i) $R_2$ and $R_3$ together represent a group of the formula A—N=, as pure E or pure Z isomers or as a mixture of both E and Z isomers, wherein A represents:
   a hydrogen atom, a hydroxy, methoxy, acetoxy, amino, methylamino or dimethylamino groups, or
   a group of the formula Y—NH— wherein Y represents either
      (a) residue of an amino acid optionally protected at the amino group as a N-benzoyl derivative or as a carbamate, or
      (b) a chain of the formula II:

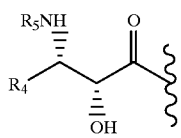

wherein:
$R_4$ is a $C_1$–$C_4$ alkyl, $C_2$–$C_5$ alkenyl, $C_3$–$C_6$ cycloalkyl group or a phenyl or heteroaryl group, optionally substituted with one, two or three substituents which may be the same or different and which are selected from a halogen atom and $C_1$–$C_4$ alkyl, $C_1$–$C_4$ alkoxy and —$CF_3$ groups;

$R_5$ is —COOR'" or —COR'" or —CONHR'" wherein R'" is $C_1$–$C_4$ alkyl, $C_2$–$C_5$ alkenyl, $C_3$–$C_6$ cycloalkyl, $C_2$–$C_4$ alkynyl or a phenyl group, optionally substituted with one, two or three substituents which may be the same or different and which are selected from a halogen atom and $C_1$–$C_4$ alkyl, $C_1$–$C_4$ alkoxy and —$CF_3$ groups; or a group of the formula Y or Y—O— wherein Y is as defined above; or (ii) $R_2$ represents a group of the formula —NH—B wherein B represents
   a) hydrogen atom,
   b) hydroxy group,
   c) amino group,
   d) a group of the formula Y—$(NH)_n$— wherein Y is as defined above and n is 0 or 1, or
   e) a group of the formula Y—O— wherein Y is as defined above;
   f) a group of the formula COR' wherein R' is as defined above, and $R_3$ represents hydrogen, taken together with R, a bond. $R_1$ is preferably a hydrogen atom, a hydroxy group or an acetoxy group; R, is preferably a hydrogen atom. $R_2$ preferably represents the group of formula NHB. B is preferably the chain of formula II.

$R_4$ is preferably phenyl or 2-furyl. $R_5$ is benzoyl or t-butoxycarbonyl group.

The pharmaceutically acceptable salts are typically those salts formed with pharmaceutically acceptable acids, both inorganic acids like hydrochloric, hydrobromic, sulfuric, phosphoric, diphosphoric, or nitric acid and organic acids such as citric, fumaric, maleic, malic, ascorbic, succinic, tartaric, benzoic, acetic, methanesulphonic, ethanesulfonic, benzenesulfonic or p-toluenesulfonic acid.

Further preferred compounds of the invention are: 13-aza-paclitaxel, 13-aza-10-desacetoxy paclitaxel, 13-aza-10-desacetyl paclitaxel, 13-aza-taxotere, 13-aza-10-deoxy-taxotere, deacetoxy-13-deoxy-13-imino paclitaxel, 10,13 dideoxy-13-imino taxotere, 13-deoxy-13-imino paclitaxel, 13-deoxy-13-imino taxotere, 10-deacetoxy-13-deoxy-13,14 ene-13-aza-paclitaxel, 13-deoxy-13,14 ene-13-aza-paclitaxel, 10,13-dideoxy-13,14 ene-13 aza-taxotere, 13,14 ene-13-aza-taxotere.

The suffix "aza" means that the oxygen atom of the substituent at position 13 of the taxol structure has been replaced with an NH residue. The present invention also provides a process for the preparation of taxane derivatives of formula I as above defined. The following scheme illustrates the reaction sequence:

Scheme I
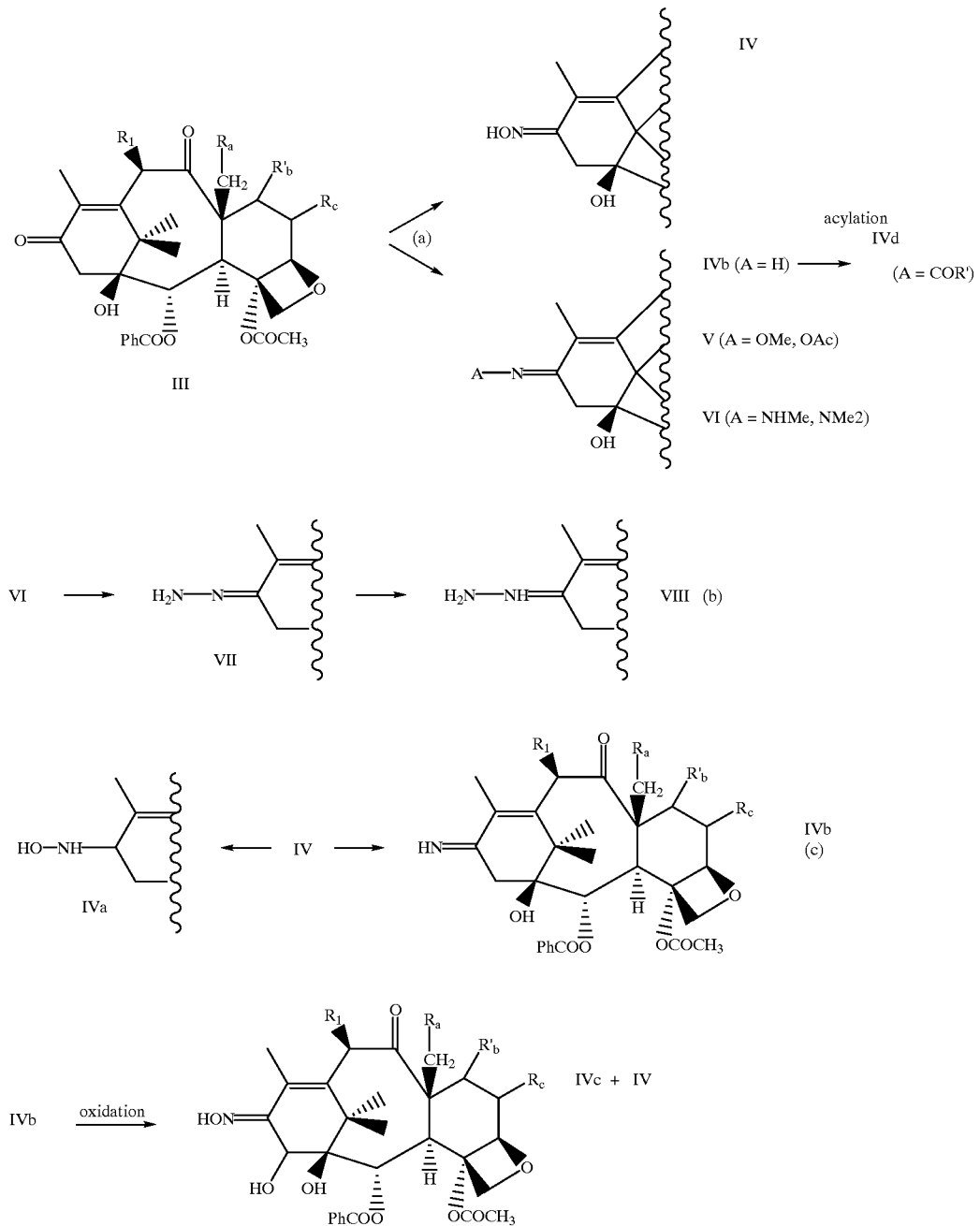

(d)

IV, IVa, IVc, V or VI —reduction→

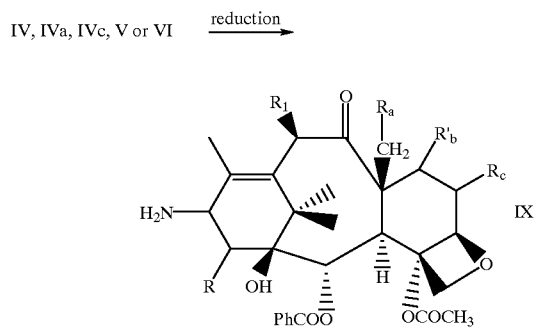

IX (e)

(IV, IVa, IVb, IVc, VII or VIII or IX ) + (Xa, Xb, Xc, or Xd or Aminoacid) ——→ XI

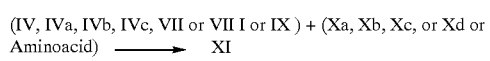

XI

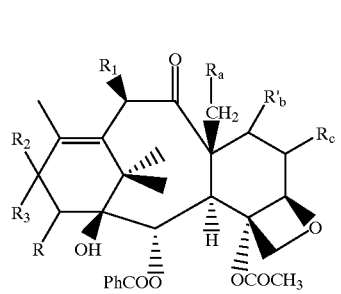

IV, IVa, IVb, IVc, IVd V, VI, VII, VIII or IX or XI —deprotection or reduction when necessary→ I (f)

XI

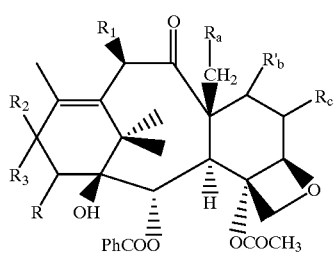

IV, IVa, IVb, IVc, IVd V, VI, VII, VIII or IX or XI —deprotection or reduction when necessary→ I (f)

The process comprises, in a first step (a), the reaction of a 7-protected-13-keto-baccatin derivative of the formula III wherein $R_1$, $R_a$ and $R_c$ are as defined above and $R'_b$ or has the same meanings of $R_b$ except for OH or $NH_2$, either represents a protected amino or hydroxy group, in which the protecting group is trialkylsilyl or other hydroxy protecting groups such as phenyldimethylsilyl, triisopropylsilyl, t-butyldimethylsilyl, dimethyl-(1-methyl, 2-methyl) propylsilyl, t-butyldiphenylsilyl, acetyl, benzyloxycarbonyl, 2,2,2-trichloroethoxycarbonyl and the like, with hydroxylamine, O-methylhydroxylamine, methylhydrazine, N,N-dimethylhydrazine, or with ammonia or an ammonium salt such as ammonium chloride, bromide or formate and optionally acylating the resulting compound thereby to give a compound of formula IV, IVb, IVd, V or VI, obtained as pure E or pure Z or as a mixture of E and Z isomers. Typically the reaction involving the 7-protected-13-keto-baccatin derivative is carried out in a solvent such as pyridine at temperatures ranging from room temperature to the boiling point of the solvent. The optional acylation of the intermediate of formula IVb may be carried out with a conventional acylating agent, such as acetic anhydride or benzoyl chloride to give a compound IVd. It is to be noted that the compound of the formula IVd may exist also as a tautomer of formula IV'd IV'd that is $R_3$ and R taken together are a bond, which can be partially reduced and deprotected to give the derivative of the formula IX as defined above.

In a second step (b), the 13-hydrazones of formula VI may be reacted with anhydrous hydrazine to give a taxane derivative of formula VII, which is then optionally reduced to a hydrazine derivative of formula VIII using standard procedures (e.g. reduction with catalytical hydrogenation such as in the presence of Raney Ni, Pt or Pd). In step (c), the resultant 13-oxime of formula IV may be partially reduced, e.g. with boranes, borohydrides or with catalytical hydrogenation such as in the presence of Raney Nickel, Pt or Pd. to give the hydroxylamino derivatives of the formula IVa or the imino derivatives of the formula IVb.

In this step, when the reduction is carried out in the presence of Ni/Raney and hydrazine, there are obtained also derivatives of the formula IVb wherein $R_1$ represents hydrogen atom. The compound of formula IVb may be oxidized in the presence of organic peracid, such as m-chloro perbenzoic acid to give again a compound of the formula IV and the derivative of formula IVc having R=OH.

In step (d), the compound of formula IV, IVa,; IVc, V or VI can optionally be reduced to give the amino derivative of formula IX using standard procedures (e.g. reduction with borohydrides or by catalytic hydrogenation).

In step (e), the C-13 derivatives of formula IV, IVa, IVb, VII, VIII or IX can be acylated with an appropriately protected amino acid (the hydroxy group, if present, will be conveniently protected, for example as O-(1-ethoxyethyl) ether or as -triethylsilyloxy) or with a molecule of the formula Xa or Xb, Xc or Xd, optionally conveniently activated at the carboxy group

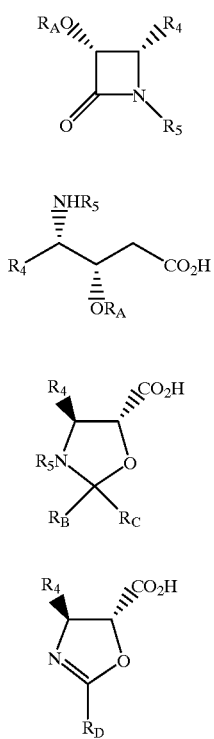

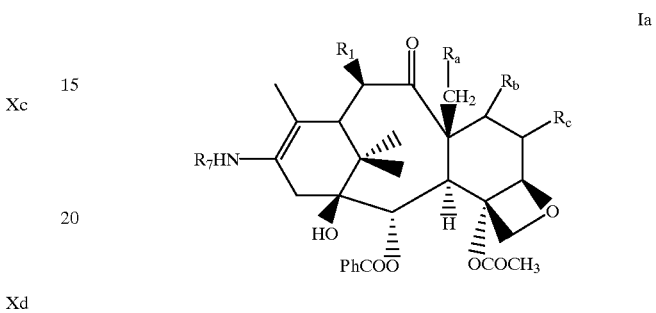

wherein $R_A$ is a hydroxy protecting group, preferably wherein $R_A$ is a hydroxy protecting group, preferably 1-ethoxyethyl, triethylsilyl, t-butyldimethylsilyl, $R_B$ is H or $CH_3$, $R_C$ is $CH_3$ or an optionally substituted phenyl group, preferably 2,4 dimethoxy or 4 methoxy phenyl group, $R_D$ is an optionally substituted phenyl group as for $R_C$ and $R_4$ and $R_5$ are as defined above, in the presence of a condensing agent such as -dicyclohexylcarbodiimide (DCC) or di-2-pyridylcarbonate (DPC), in toluene and 4-dimethylaminopyridine (DMAP) or -sodium hexamethyldisilazide (NaHMDS) in tetrahydrofurane (THF) to give the protected intermediate of the formula XI.

The useful intermediate derivatives of the formulas IV, IVa, IVb, IVc, IVd, IV'd, V, VI, VII VIII, IX and XI are also novel and are within the scope of the invention.

In the final optional step (f), the compounds of the formula IV, IVa, IVb, IVc, IVd, V, VI, VII, VII, IX and XI are then deprotected and if wanted reduced, when $R_b'$ is azido group, to give the said taxane derivative of the formula I. In this final step, when $R_b'$ is a protected amino or hydroxy group, the deprotection is carried out for example by treatment with $(n-Bu)_4NF$, HF/Pyridine, HF/MeCN, Zn/AcOH. When the acylating groups employed in step (e) were protected, the protecting groups are conveniently removed by appropriate methods,in the last step (f), for example when the acylating molecule of formula $X_c$, as above defined, is used, the protecting group is removed in acidic conditions, such as with HCl/MeOH or EtOH, HCOOH 99%, $CF_3CO_2H$ organic solvent ($CH_2Cl_2$). The resultant compounds of the formula I may also be converted into different compounds of the formula I by appropriate known reactions, after necessary protections, for example the compounds of formula I wherein $R_a=R_c=H$, and $R_b$ is OH, may be converted into a compound of formula I wherein $R_a$ and $R_b$ taken together form a bond by protection of the hydroxy group, reaction with triflic anhydride and treatment with a base. The preparation of the starting compounds of the formula III, Xa, Xb, Xc and Xd are known or may be carried out according to known methods; for example 7-triethylsilyl-3-keto-baccatin (III, R=triethylsilyl, $R_1=OCOCH_3$) has already been described [see J.Chem.Soc., Chem.Commun., (1994), 295, Chem. Comm. (1970), 216 , J.A.C.S.,(1971),93, 2325, Tetrahedron Asymmetry 1992, 3, 1007, JOC 1991, 56, 1681, Tetrahedron 1992,48, 6985, Tetrahedron Letters 1992, 33, 5185, JOC 1993, 58, 1287, EP-A 400971, 1990.]In a further aspect, the present invention also provides a compound of formula Ia

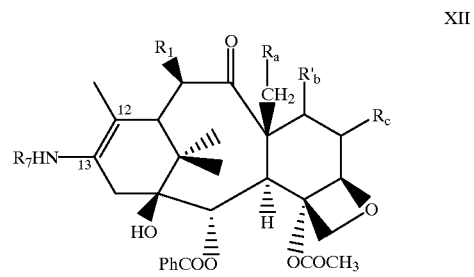

wherein $R_a$, $R_b$, $R_c$ and $R_1$ are as above defined, $R^7$ is hydrogen atom or an acyl residue of formula COR' or Y, wherein Y and R' are defined above and the pharmaceutically acceptable salt thereof.

The compound of formula Ia and the pharmaceutically acceptable salt thereof may be prepared by a process which comprises: (a) reducing a compound of the formula IVb as above defined, optionally in the presence of an acylating agent, to give a compound of formula XII

XII wherein $R_1$, $R_a$, $R_b'$, $R_c$ and $R_7$, are as above defined except that $R_7$ is not a hydrogen atom, b) deprotecting the resultant compound of the formula XII to give a compound of formula Ia and c) optionally salifying the thus obtained compound of formula Ia to give a pharmaceutically acceptable salt thereof.

Step (a) may be effected by using standard conditions such as reduction with a borohydride such as sodium cyanoborohydride or catalytic hydrogenation.

Step (b) can be carried out as described above for step (f) The appropriate acylating agent may be selected from the group of activated/protected carboxylic acid derivatives, such as acetic anhydride, benzoyl chloride, cinnamoyl chloride, isobutanoylchloride and the like.

BIOLOGICAL ACTIVITY

The cytotoxic activity of the compounds may be evaluated on $B_{16}$-$F_{10}$ murine melanoma cell line which was responsive to paclitaxel. The mode of action of the compound may also be tested on the tubulin assembly-disassembly assay in comparison with taxol a reference compound.

(A) In vitro drug sensitivity assay.

Exponentially growing $B_{16}$-$F_{10}$ murine melanoma cells were seeded ($2\times10^4$/ml) in RPMI 1640 medium supplemented with 10% heat-inactivated fetal calf serum and 2 mM glutamine in 24-well plates (Costar). Scaled concentrations of tested compounds were added immediately after seeding. The inhibition of cell growth was evaluated by counting cells with a Coulter counter after 24 hrs incubation. For each tested compound concentration triplicate cultures were used. The antiproliferative activity of the tested compounds was calculated from dose-response curves and expressed as $IC_{50}$ (dose causing 50% inhibition cell growth in treated cultures relative to untreated controls).

(B) Microtubule assembly-disassembly assay.

Calf brain tubulin was prepared by two cycles of assembly-disassembly (Shelanski M. L., Gaskin F. and Cantor C. R., Proc.Natl.Acad.Sci. U.S.A. 70, 765–768, 1973) and stored in liquid nitrogen in MAB (0.1 M MES, 2.5 mM EGTA, 0.5 mM $MgSO_4$ 0.1 mM EDTA, 0.1 mM DTT pH 6.4). All the experiments were carried out on protein stored for less than 4 weeks. Before each experiment, the tubulin was kept 30 min at 4° C. Assembly was monitored by the method of Gaskin et al. (Gaskin F., Cantor C. R. and Shelanski M. L., J.Molec.Biol. 89, 737–758, 1974).

The cuvette (1 cm path) containing tubulin (1 mg/ml) and 1 mM GTP was shifted to 37° C. and continuous turbidity measurements were made at 340 nm on a Perkin-Elmer 557 double wavelength, double beam spectrophotometer equipped with an automatic recorder and a thermostatically regulated sample chamber. After 30 minutes, 4 mM $CaCl2$ was added and depolymerisation was measured for 10 minutes as decreased turbidity. At regular intervals of 15 minutes scaled doses of the tested compounds were added and variations in the turbidity were monitored. Data are expressed as percentage of repolymerization induced by the tested compounds.

The taxane derivatives of formula I and Ia are thus antitumour agents. They may also be useful for the preparation of other antitumour agents. A human or animal suffering from a tumour may thus be treated by a method which comprises the administration thereto of an effective amount of a taxane derivative of formula I or Ia or a pharmaceutically acceptable salt thereof according to the invention. The condition of the human or animal may thereby be improved. Examples of tumours that can be treated are sarcomas, carcinomas, lymphomas, neuroblastomas, melanomas, myelomas, Wilms tumour, leukemias and adenocarcinomas. Taxane derivatives of formula I or Ia pharmaceutically acceptable salts thereof can be used to treat ovarian cancer, platinum-resistant ovarian cancer, metastatic breast cancer, non-small cell lung cancer, and head and neck cancer. The invention also provides a pharmaceutical composition which comprises, as active ingredient, a compound of formula I or Ia or a pharmaceutically acceptable salt thereof according to the invention and a pharmaceutically acceptable carrier or diluent. The composition of the invention is usually prepared following conventional methods and is administered in a pharmaceutically suitable form. Administration can be made by any of the accepted ways for administration of antitumour agents such as intravenous, intramuscular or subcutaneous injection or topical application. For systemic injection the active compound may be, e.g., dissolved in a vehicle consisting of a mixture of polyoxyethylated castor oil (Chremophor EL) 50% and ethanol 50% and then diluted with glucose 5% solution at the desired concentration, or in other pharmaceutically suitable carriers. The amount of the active compound administered depends on the treated subject, age, weight, sex etc., and the severity of the affliction. The method of administration depends on the judgement of the prescribing physician. A suitable dosage for an average 70 kg person may range from about 0.01 g to about 1 g per day.

The following Examples illustrate the invention but they are not intended to limit it thereto.

EXAMPLE 1

(E)-7-O-triethylsilyl-13-deoxy-13-oxymino-baccatin

7-O-triethylsilyloxy-13-keto-baccatin (260 mg, 0.37 mmol) and hydroxylamine hydrochloride (130 mg, 1.87 mmol) were dissolved in pyridine (3 mL) and heated to reflux for 12 hours. After evaporating pyridine under vacuum, the residue was dissolved in ethyl acetate, washed with 0.5N HCl (×2), with water, dried over $Na_2SO_4$ and concentrated to give a crude product, containing the (E)-oxime, the (Z)-oxime and some starting ketone. The oximes were separated on silica gel (eluant n-hexane/ethyl acetate 3:1).

The (E)-oxime was isolated as a white solid (100 mg, 38% yield). TLC (n-hexane/ethyl acetate 1:1); Rf=0.54. $^1$H NMR ($CDCl_3$, 400 MHz) :0.5–0.7 (m, 6H, Si $(CH_2CH_3)_3$), 0.92 (t,J=8.0 Hz, 9H,Si$(CH_2CH_3)_3$), 1.08 (s,3H,17), 1.23 (s,3H, 16), 1.66 (s,3H,19), 1.75 (s,1H,OH-1), 1.87 (m,1H,6β), 2.21 (s,3H,$COCH_3$-10), 2.22 (s,3H,$COCH_3$-4), 2.26 (s,3H,18), 2.54 (m,1H,6α), 2.78 (d,J=19.6 Hz,1H,14-β), 3.02 (d,J=19.6 Hz,1H,14-α), 3.80 (d,J=6.7 Hz,1H,3), 4.13 (d, J=8.4 Hz,1H, 20β), 4.32 (d, J=8.4 Hz, 1H,20α), 4.49 (dd,J=6.8,10.5 Hz,1H,H-7), 4.94 (dd,J=9.4,1.8 Hz,1H,H-5), 5.67(d,J=6.7 Hz, 1H,2), 6.61 (s,1H,10), 7.4–8.2 (m,5H,phenyl), 8.8 (bs, 1H,NOH).

EXAMPLE 2

(Z)-7-O-triethylsilyl-13-deoxy-13-oxymino-baccatin

The (Z)-oxime was isolated as a white solid (30 mg, 11% yield), (see example 1)

TLC (n-hexane/ethyl acetate 1:1); Rf=0.30. $^1$H-NMR(400 MHz, $CDCl_3$) :0.60 (m, 6H, Si$(CH_2CH_3)_3$), 0.92 (m,9H,Si $(CH_2CH_3)_3$), 1.13 (s,3H,17), 1.21 (s,3H,16), 1.66 (s,3H,19), 1.79 (s,1H,OH-1), 1.90 (m,1H,6β), 2.18 (s,3H,$COCH_3$-10), 2.23 (s,3H,$COCH_3$-4), 2.43 (s,3H,18), 2.54 (d, J=17.6 Hz,1H,14β), 2.56 (m,1H, 6α), 3.10 (d, J=17.6 Hz,1H,14α), 3.76 (d, J=6.4 Hz,1H,3), 4.17 (d, J=8.5 Hz,1H,20β), 4.34 (d, J=8.5 Hz, 1H, 20α), 4.54 (dd, J=6.7 Hz,1H,7), 4.98 (dd, J=1.5, 9.4 Hz,1H,5), 5.65 (d, J=6.4 Hz,1H,2), 6.61 (s, 1H,10), 7.4–8.1 (m,5H,phenyl).

EXAMPLE 3

(E)-13-deoxy-13-oxymino-baccatin

To 7-O-triethylsilyloxy-13-deoxy-13-(E)oxymino-baccatin (80.4 mg, 0.11 mmol), dissolved in dry tetrahydrofurane (5 mL), and stirred at 0° C. under nitrogen, tetrabutylammonium fluoride (70 mL) was added, the reaction mixture was let to warm up to room temperature and stirred for 14 hours. The mixture was diluted with ethyl acetate, washed with water, then with brine and dried over $Na_2SO_4$. After concentration 62 mg (0.1 mmol, 90% yield) of desired compound was obtained.

TLC (n-hexane/ethyl acetate 1:1.5); Rf=0.32. $^1$H NMR (CDCl3, 400 MHz) :1.14 (s,6H,16+17), 1.66 (s,3H,19), 1.75 (s,1H,OH-1), 1.87 (m,1H,6β), 2.14, 2.20, 2.27 (three singlets,9H, $COCH_3$-10+$COCH_3$-4+18), 2.56 (m,2H,6α+

OH-7), 2.80 (d,J=19.6 Hz,1H,14-β), 3.04 (d,J=19.6 Hz,1H, 14-α), 3.81 (d,J=6.7 Hz,1H,H-3), 4.14 (d,J=8.2 Hz,1H,20β), 4.32 (d,J=8.2 Hz,1H,20β), 4.46 (m,1H,7), 4.97 (dd,J=2.0, 9.7 Hz, 1H,5), 5.66(d,J=6.7 Hz,1H,2), 6.45 (s,1H,10), 7.4–8.2 (m,5H,phenyl), 8.0 (bs,1H,NOH). FAB-MS=m/Z 598 [M–H]

EXAMPLE 4

(Z)-13-deoxy-13-oxymino-baccatin

To 7-O-triethylsilyloxy-13-deoxy-13-(Z)-oxymino-baccatin (77.3 mg, 0.108 mmol), dissolved in pyridine (2.5 mL) and stirred at 0° C. under nitrogen, 70% HF pyridine complex (0.25 mL) was added, the reaction mixture was let to warm up to room temperature and stirred for 6 hours. Additional HF pyridine complex (0.125 mL) was added and the mixture stirred at room temperature 2 hours longer. After concentration under vacuum, 66 mg of crude material was obtained. Purification by chromatography (silica gel, eluant=pet.ether/ethyl acetate 7:8) yielded the desired product, as a white solid (40.7 mg, 63% yield).

TLC (n-hexane/ethyl acetate 1:1.5), Rf=0.22. $^1$H-NMR (400 MHz, CDCl$_3$) :1.13 (s,3H,16), 1.21 (s,3H,17), 1.66 (s,3H,19), 1.89 (m,1H,6β), 2.24, 2.26, 2.32 (three singlets, 9H, COCH$_3$-4+COCH$_3$-10+18), 2.59 (m, 3H,OH-7+14β+6α), 3.10 (d, J=17.6 Hz,1H,14α), 3.72 (d, J=6.7 Hz,1H,3), 4.17 (d, J=8.2 Hz,1H,20β), 4.34 (d, J=8.2 Hz,1H,20α), 4.50 (m,1H,7), 5.02 (dd, J=2.1, 9.6 Hz,1H,5), 5.65 (d, J=6.7 Hz,1H, 2), 6.44 (s,1H, 10), 7.4–8.1 (m, 5H, phenyl). FAB-MS: m/Z 598[M–H]

EXAMPLE 5

(E)-13-deoxy-13-O-[(S)-N-(tertbutoxycarbonyl)-α-phenylglycyl]-oxymino baccatin and (E)-13-deoxy-13-O-[(R)-N-(tertbutoxycarbonyl)-α-phenylglycyl]-oxymino-baccatin A solution of (E)-13-deoxy-13-oxymino-baccatin (117 mg, 0.195 mmol), 1,3-dicyclohexylcarbodiimide (DCC, 100 mg, 0.48 mmol), (S)-BOC-L-α-phenyl-glycine (100 mg, 0.4 mmol), N,N-dimethyl pyridine (DMAP, cat. amount) in toluene (12 mL) was stirred at room temperature for 7 hours, the reaction mixture was filtered and concentrated to give a crude product (255 mg) that was purified by chromatography (silica gel, eluant: n-hexane/ethyl acetate 1.5:1) and then by preparative TLC (eluant: n-hexane/ethyl acetate 1:1). Two products were obtained, identical except for the stereochemistry of the carbon in the side chain: isomer 1 (24 mg, 15%), isomer 2 (31 mg, 19%).

Isomer 1: TLC (n-hexane/ethyl acetate 1:1); Rf=0.34. $^1$H-NMR (400 MHz, CDCl$_3$) : 1.05 (s,3H,17), 1.11 (s,3H, 16), 1.45 (s, 9H, t-Bu), 1.62 (s,3H,19), 1.78 (bs,1H,OH-1), 1.84 (m,1H,6β), 1.95 (s, 3H,CH$_3$CO-4), 2.21 (s,3H,18), 2.27 (s, 3H,CH$_3$CO-10), 2.54 (m, 2H, 6α+OH-7), 2.66 (d,J=19.9 Hz,1H,14β), 3.02 (d, J=19.9 Hz, 1H,14α), 3.76 (d, J=6.7 Hz,1H,3), 4.08 (d, J=8.5 Hz, 20β), 4.31 (d,J=8.5 Hz,20α), 4.44 (dd, J=6.7,10.5 Hz,1H, 7), 4.91 (d,J=8.5 Hz,1H,5), 5.50 (d, J=7.4 Hz,1H, NH-3'), 5.56 (d, J=7.4 Hz,1H, 2'), 5.61 (d, J=6.7 Hz,1H,2), 6.42 (s,1H, 10), 7.2–8.2 (m, 10H, two phenyls). (FAB-MS=m/z 834 (M+H)

Isomer 2=TLC (n-hexane/ethyl acetate 1:1); Rf=0.29. $^1$H-NMR (400 MHz, CDCl$_3$) : 1.11 (S, 3H, 17), 1.12 (s, 3H,16), 1.25 (s, 3H, COCH$_3$-4), 1.42 (s, 9H, t-Bu), 1.60 (s, 3H, 19), 1.80 (m, 1H, 6β), 1.85 (s, 1H, OH-1), 2.19 (s, 3H, 18), 2.27 (s, 3H, COCH$_3$-10), 2.49 (m, 2H, 6α+OH-7), 2.87 (s, 2H,14), 3.70 (d, d, J=6.7 Hz,1H,3), 4.04 (d, J=8.5 Hz,1H,20β), 4.23 (d,J=8.5 Hz,1H,20α), 4.39 (dd, J=6.7,10.8 Hz,1H,7), 4.83 (dd, J=1.9,9.5 Hz,1H,5), 5.48 (d, J=7.0 Hz,1H,2'), 5.60 (d, J=6.7 Hz,1H,2), 5.65 (d, J=7.0 Hz,NH-3'), 6.40 (s,1H, 10), 7.3–8.1 (m,10H, two phenyls). FAB-MS: m/z 834 (M+H)

EXAMPLE 6

(Z)-13-deoxy-13-O-[(S)-N-(tertbutoxycarbonyl)-α-phenylglycyl]-oxymino-baccatin A solution of (Z)-13-deoxy-13-oxymino-baccatin (37 mg, 0.06 mmol), DCC (24 mg, 0.12 mmol), BOC-L-α-phenylglycine (20 mg, 0.08 mmol), DMAP (cat. amount) in toluene (4 mL) was stirred at room temperature for 2.5 hours. The reaction mixture was filtered and concentrated to give a crude product (76 mg) that was purified by chromatography (silica gel, eluant:n-hexane/ethyl acetate 11:14) to yield the title product as a white solid (30 mg, 60% yield).

TLC (n-hexane/ethyl acetate 1:1); Rf=0.27. $^1$H-NMR(400 MHz, CDCl$_3$) :1.06 (s,3H,17), 1.10 (s,3H,16), 1.45 (s, 9H, t-Bu), 1.65 (s,3H,19), 1.75 (s,1H,OH-1), 1.88 (m,1H, 6β), 2.18 (s,3H,18),2.20 (s,3H,COCH$_3$-4), 2.28 (s,3H,COCH$_3$-10), 2.43 (d, J=4.1 Hz,1H,OH-7), 2.57 (m,1H,6α), 2.79 (d,J=18.2 Hz,1H 14β), 3.18 (d,J=18.2 Hz,1H,14α), 3.64 (d,J=6.6 Hz,1H,3), 4.16 (d,J=8.5 Hz,1H,20β), 4.32 (d,J=8.5 Hz,1H,20α),4.45 (m,1H,7), 4.97 (dd,J=2.2, 9.5 Hz,1H,5), 5.50 (m,2H, 2'+NH-3'), 5.62 (d,J=6.6 Hz,1H,2), 6.37 (s,1H, 10), 7.2–8.1 (m,10H,two phenyls). FAB-MS:m/Z 834 (M+H)$^+$

EXAMPLE 7

7-O-triethylsilyl-13-deoxy-13-imino-baccatin

To a solution of 7-O-triethylsilyloxy-13-oxymino-baccatin (mg100, 0.14 mmol) and 51% hydrazine hydrate (350 mL) in ethanol (7 mL), Aldrich W-2 Raney-nickel (100 mg, as aqueous slurry, after washing with water and ethanol) was added. The reaction mixture was stirred at room temperature for 12 hours, then was filtered through celite and purified by preparative TLC (eluant: n-hexane/ethyl acetate 1:4) to give the title compound (25 mg, 25% yield) as a white solid.

TLC (n-hexane/ethyl acetate 1:4); Rf=0.32. $^1$H-NMR (400 MHz, CDCl$_3$) :0.59 (m, 6H, Si(CH$_2$CH$_3$)$_3$), 0.92 (t, J=7.8 Hz, 9H, Si(CH$_2$CH$_3$)$_3$), 1.11 (s,3H,17), 1.25 (s,3H, 16), 1.66 (s,3H,19), 1.87 (m,1H,6β), 2.19, 2.21, 2.28 (three singlets, 9H,CH$_3$CO-4+CH$_3$CO-10+18), 2.52 (m,1H,6α), 2.69 (d,J=19 Hz, 1H, 14b), 3.10 (d, J=19 Hz,1H,14α), 3.88 (d,J=6.8 Hz,1H,3), 4,14 (d, J=8.5 Hz,1H,20β), 4.31 (d,J=8.5 Hz,1H,20α), 4.48 (m, 1H,7), 4.93 (d, J=9.7 Hz,1H,5), 5.66 (d, J=6.8 Hz,1H,2), 6.60 (s,1H,10), 7.5–8.1 (m,5H, phenyl)

EXAMPLE 8

7-O-triethylsilyl-10-deacetoxy-13-deoxy-13-imino-baccatin

To a solution of 7-O-triethylsilyloxy-13-oxymino-baccatin (50 mg, 0.07 mmol) and 51% hydrazine hydrate (158 mL) in ethanol (3 mL), Raney-nickel aqueous slurry (50 mg) was added. The reaction mixture was stirred at room temperature for 3 hours, then was filtered through celite and purified by preparative TLC (eluant:n-hexane/ethyl acetate 1:4) to give the title compound (40 mg, 90% yield) as a white solid.

TLC (n-hexane/ethyl acetate 1:4); Rf=0.22. $^1$H-NMR(400 MHz, CDCl$_3$) :0.58 (m,6H,Si(CH$_2$CH$_3$)$_3$), 0.95 (t, J=7.9

Hz,9H,Si(CH$_2$CH$_3$)$_3$), 1.13 (s,3H,17), 1.19 (s,3H,16), 1.59 (s,3H,19), 1.86 (m,1H,6β), 2.07 (d, J=1.2 Hz,3H, 18), 2.20 (s, 3H,OCOCH$_3$), 2.50 (m,1H, 6α), 2.68 (d,J=18.7 Hz,1H, 14β), 3.09 (d,J=18.7 Hz,1H, 14α), 3.60 (dq,J=14.5,1.2 Hz,1H,10β), 3.93 (d,J=14.5 Hz,1H,10α), 4.07 (d,J=6.5 Hz,1H,3), 4.12 (d, J=8.2 Hz,1H,20β), 4.31 (d,J=8.2 Hz;1H, 20α), 4.50 (dd,J=6.7,10.5 Hz,1H,7), 4.93 (d,J=7.6 Hz,1H,5), 5.64 (d, J=6.5 Hz,1H,2), 7.4–8.1 (m,5H, phenyl). FAB-MS= m/z 640 [M+H][30]

EXAMPLE 9

10-Deacetoxy-13-deoxy-13-imino-baccatin

To a solution of 7-O-triethylsilyl-10-deacetoxy-13-deoxy-13-imino-baccatin (34 mg, 0.053 mmol) in THF (4 mL) at 0° C., a 1M solution of tetrabutylammonium fluoride in THF (60 μL) was added and the reaction mixture was stirred for 2 hours at 0° C. The reaction mixture was poured into ice-water and extracted with ethyl acetate. The organic layer was washed with brine, water, dried over Na$_2$SC$_4$ and concentrated under vacuum. The crude product was purified by silica gel chromatography (eluant:dichloromethane/methanol 19:1) yielding 24 mg of the title compound (86%);

TLC (dichloromethane/methanol 19:1); Rf=0.27. $^1$H-NMR (400 MHz, CDCl$_3$) :1.14 (s,3H,17); 1.19 (s,3H, 16); 1.61 (s, 3H,19); 1.78 (m,1H, 6); 2.06 (d, J=1.2 Hz,3H, 18); 2.20 (s, 3H,CH$_3$CO); 2.63 (m,1H,6α); 2.69 (dd, J=18.8, 1.1 Hz,1H,14β); 3.12 (d, J=18.8 Hz,1H,14α); 3.67 (dq, J=14.9,1.2 Hz,1H,10); 4.00 (d, J=14.9 Hz,1H,10α); 4.14 (m, 2H,20β+3); 4.36 (m,2H, 20α+7); 4.95 (dd, J=9.4, 2.1 Hz,1H,5); 5.68 (dd, J=6.8, 1.1 Hz,1H,2); 7.4–8.1 (m,5H, phenyl)

EXAMPLE 10

7-O-triethylsilyl-11-hydro-12,13 ene-13-deoxy-13-amino-baccatin

A solution of 7-O-triethylsilyloxy-13-deoxy-13-imino-baccatin (60 mg, 0.086 mmol), para-toluensulfonic acid (10 mg), NaBH$_3$CN (60 mg) in methanol (1 mL) was stirred at room temperature for 30 minutes. The reaction mixture was concentrated, dissolved in ethyl acetate, the organic layer was washed with brine and water, dried over Na$_2$SO$_4$ and concentrated to give the desired product (60 mg, quant.).

TLC (n-hexane/ethyl acetate 2:3); Rf=0.45. $^1$H-NMR(400 MHz, CDCl$_3$) :0.54 (m, 6H, Si(CH$_2$CH$_3$)$_3$), 0.89 (t, J=7.9 Hz, 9H, Si(CH$_2$CH$_3$)$_3$) 1.08 (s,3H,16), 1.12 (s,3H,17), 1.60 (s,3H,19), 1.72 (s,3H,18), 1.85 (m,1H, 6β), 1.93 (m,1H, 14β), 2.17, 2.33 (two singlets, 6H, CH$_3$CO-4+CH$_3$CO-10), 2.41 (s, 1H, 13), 2.49 (m,1H, 6α), 2.66 (d,J=17.3 Hz,1H, 14α), 4.18 (d,J=5.5 Hz,1H,3), 4.24 (d,J=8.5 Hz,1H,20α), 4.40 (m,2H,20β+7), 4.91 (dd,J=2.3, 9.7 Hz,1H,5), 5.50 (dd, J=1.8, 5.5 Hz,1H,2), 5.95 (s,1H,10), 7.4–8.1(m,5H,phenyl). FD-MS=m/Z 699

EXAMPLE 11

7-O-triethylsilyl-10-deacetoxy-11-hydro-12,13 ene-13-deoxy-13-amino-baccatin

A solution of 7-O-triethylsilyloxy-10-deacetoxy-13-deoxy-13-imino-baccatin (26 mg, 0.037 mmol), para-toluensulfonic acid (2 mg), NaBH$_3$CN (mg35) in methanol (2 mL) was stirred at room temperature for 20 minutes. The reaction mixture was concentrated, dissolved in ethyl acetate, the organic layer was washed with brine and water, dried over Na$_2$SO$_4$ and concentrated to give the desired product (20 mg, 84% yield).

TLC (n-hexane/ethyl acetate 2:3); Rf=0.5. $^1$H-NMR (400 MHz, CDCl$_3$) :0.52 (m,6H,Si(CH$_2$CH$_3$)$_3$), 0.90(t, J=7.9 Hz,9H,Si(CH$_2$CH$_3$)$_3$), 1.10(s,3H,17), 1.15(s,3H,16), 1.59(s, 3H,19), 1.86(m,1H,6β), 1.89(m,1H,14β), 2.04(s,3H,18), 2.20(s,3H,OCOCH$_3$), 2.43(s,1H,13), 2.50(m,1H,6α), 2.69 (d,J=18.7 Hz,1H,14α), 3.55 (dq, J=14.5, 20 1.2 Hz,1H,10β), 3.89(d,J=14.5 Hz,1H,10α), 4.08(d,J=6.5 Hz,1H,3), 4.12(d, J=8.2 Hz,1H,20α), 4.31 (d, J=8.2 Hz,1H,20β), 4.50(m,1H, 7), 4.93(d,J=7.6 Hz,1H,5), 5.64(d,J=6.5 Hz,1H,2), 7.4–8.1 (m, 5H,phenyl). FD-MS:m/Z 641

EXAMPLE 12

7-O-triethylsilyl-13-deoxy-13-acetylimino-baccatin

To a solution of 7-0-triethylsilyl-13-deoxy-13-imino-baccatin (10 mg, 0.014 mmol) in THF (1 mL) at 0° C., acetic anhydride (6 μL) was added. After 30 minutes stirring at 0° C. the reaction mixture was poured into cold water and extracted with ethyl acetate. The organic phase was washed with brine and water, dried over Na$_2$SO$_4$ and concentrated to give the title compound (85% yield). TLC (n-hexane/ethyl acetate 1:1); Rf=0.58.

EXAMPLE 13

7-O-triethylsilyl-10-deacetoxy-13-deoxy-acetylimino-baccatin

To a solution of 7-O-triethylsilyl-10-deacetoxy-13-deoxy-13-imino-baccatin (200 mg, 0.3 mmol) in THF (12 mL) at 0° C., acetic anhydride (125μL) was added. After 30 minutes stirring at 0° C. the reaction mixture was poured into cold water and extracted with ethyl acetate. The organic phase was washed with brine and water, dried over Na$_2$SO$_4$ and concentrated to give the title compound (80% yield).

TLC (n-hexane/ethyl acetate 1:1); Rf=0.6. $^1$H-NMR (400 MHz, CDCl$_3$) : 0.5–0.7(m,6H,Si(CH$_2$CH$_3$)$_3$); 0.95 (m,9H, Si(CH$_2$CH$_3$)$_3$); 1.16 (s,3H,17); 1.19 (s,3H,16); 1.60 (s,3H, 19); 1.86 (m,1H,6β); 2.04 (s,3H,18); 2.18(s,3H,COCH$_3$-4); 2.27 (d,J=19.0 Hz,1H,14); 2.40 (s,3H,NCOCH$_3$); 2.60 (m,1H,6α); 3.22 (d, J=19.0 Hz,1H,14α); 3.58 (d, J=14.4 Hz,1H,10β); 3.96 (d,J=14.4 Hz,1H,10α); 4.09 (m,2H,3+ 20β); 4.30 (d,J=8.5 Hz, 1H,20α); 4.53 (dd,J=10.5; 7.0 Hz,1H,7); 4.90 (m,1H,5); 5.64 (d,J=6.2 Hz,1H,2); 7.4–8.1 (m,5H,phenyl);

The title compound may be in equilibrium with the following tautomeric form:

7-O-triethylsilyl-10-deacetoxy-13-deoxy-13,14-ene-13-acetylamino-baccatin $^1$H-NMR (400 MHz, CDCl$_3$) : 0.5–0.7 (m,6H,Si (CH$_2$CH$_3$)$_3$); 0.95 (m,9H,Si(CH$_2$CH$_3$)$_3$); 1.11 (s,3H,16); 1.25 (s, 3H,17); 1.66 (s,3H,19); 1.90 (m,1H,6β); 1.93 (s,3H, 18); 2.11 (s,3H, COCH$_3$-4) 2.17 (s,3H,NCOCH$_3$); 2.47 (m, 1H, 6α); 3.54 (d,J=14.7 Hz, H,10β); 3.74 (d, J=14.7 Hz,1H, 10α); 3.86 (d,J=7.0 Hz,1H,3); 4.21,4.27 (two doublets,J=8.2 Hz,2H,20); 4.39 (dd,J=10.2,6.7 Hz,1H,7); 4.90 (dd,J=9.4, 2.0 Hz,1H,5); 5.79 (d, J=7.0 Hz,1H,2); 6.34 (s,1H,14); 6.74 (s,1H,NHCOCH$_3$); 7.4–8.1 (m,5H,phenyl);

EXAMPLE 14

7-O- triethylsilyl-10-deacetoxy-11-hydro-12,13 ene-13-deoxy-13-acetylamino-baccatin To a solution of 7-O-triethylsilyl-10-deacetoxy-13-deoxy-13-imino-baccatin (36 mg, 0.056 mmol) in THF (2.4 mL) at room temperature, acetic anhydride (120 μL) and NaBH₃CN (72 mg) were added. After 40 minutes at room temperature, the reaction mixture was poured into cold water and extracted with ethyl acetate. The organic phase was washed with brine and water, dried over Na₂SO₄ and concentrated to give a crude product that was chromatographed on preparative TLC (eluant: n-hexane/ethyl acetate 3:7). The title compound was obtained in 56% yield. TLC (n-hexane/ethyl acetate 1:1); Rf=0.17. ¹H-NMR (600 MHz, CDCl₃) : 0.5–0.7 (m,6H,Si(CH₂CH₃)₃); 0.8–1.0 (m,9H,Si(CH₂CH₃)₃) 1.12 (s,3H,16); 1.21 (s,3H,17); 1.52 (s,1H,OH-1); 1.58 (s,3H,19); 1.73 (s,3H,18); 1.89 (m,1H,6β); 2.10 (s,3H,CH₃CONH); 2.34 (s,3H, CH₃CO-4); 2.42 (m, 1H,6α); 2.57 (m, 2H,11+14α); 2.83 (d, J=13.4 Hz,1H,10α); 2.96 (m,2H,10β+14β); 3.78 (d,J=5.2 Hz,1H, 3); 4.22 (dd, J=7.1,10.7 Hz,1H,7); 4.30, 4.36 (two doublets, J=8.5 Hz,2H,20); 4.89 (m,1H,5); 4.47 (dd, J=5.2, 1.1 Hz,1H,2); 6.52 (s,1H,CONH); 7.4–8.1 (m,5H,phenyl). FAB-MS=m/z 683

EXAMPLE 15

10-Deacetoxy-11-hydro-12,13 ene-13-deoxy-13-acetylamino-baccatin

To a solution of 7-O-triethylsilyl-10-deacetoxy-13-deoxy-12,13 ene-13-acetylamino-baccatin (44 mg, 0.064 mmol) in THF (4 mL) at 0° C., 1M tetrabutylammonium fluoride solution in THF (2×70 μL) was added in two portions. After 2 hours at 0° C., the reaction mixture was poured into cold water and extracted with ethyl acetate. The organic phase was washed with brine and water, dried over Na₂SO, and concentrated to give a crude product that was chromotographed on preparative TLC (eluant: n-hexane/ethyl acetate 1:4). The title compound was obtained in 75% yield. TLC (n-hexane/ethyl acetate=1:4); Rf=0.1 ¹H-NMR (400 MHz, CDCl₃) :1.11 (s,3H,16); 1.20 (s,3H,17); 1.61 (s,3H,19); 1.72 (s,3H,18); 1.83 (m,1H,6β); 2.10 (s, 3H,CH₃CONH); 2.34 (s,3H,CH₃CO-4); 2.55 (m,3H,6α+11+14α); 2.87 (dd,J=13.8 Hz,J=2.0 Hz,1H,10α); 2.97 (d,J=18.2 Hz,1H,14β); 3.06 (dd, J=13.8, 11.4 Hz,1H,10β); 3.76 (d, J=5.3 Hz,1H,3); 4.12 (m,1H,7); 4.32, 4.37 (two doublets, J=8.5 Hz,2H,20); 4.90 (dd,J=9.4, 2.6 Hz,1H,5); 5.56 (d, J=5. 3 Hz, 1H, 2); 6.53 (s, 1H, CH₃CONH); 7.4–8.1 (m, 5H, phenyl).

EXAMPLE 16

7-O-triethylsilyl-10-deacetoxy-13-deoxy-13-oxymino-14(β)-hydroxy-baccatin

To a solution of 7-O-triethylsilyl-10-deacetoxy-13-deoxy-13-imino-baccatin (55 mg, 0.086 mmol) in dichloromethane (3 mL), 50% metachloro perbenzoic acid (52 mg) was added and the reaction mixture stirred at room temperature for 1 hour. More dichloromethane (20 mL) was added and the solution was extracted with sat.solution of sodium hydrogencarbonate (4×25 mL) and then washed with brine. The crude product was chromatographed on preparative TLC (eluant=n-hexane/ethyl acetate 1:1). The title compound was obtained in 25% yield. Also the 13-oximino derivatives, described in Example 1, were isolated.

TLC (n-hexane/ethyl acetate 1:1); Rf=0.55. ¹H-NMR (400 MHz, CDCl₃) : 0.5–0.7 (m, 6H, Si (CH₂CH₃)₂); 0.95 (m, 9H, Si (CH₂CH₃)₃; 1.11 (s,3H,17); 1.21 (s,3H,16); 1.64 (s,3H,19); 1.88 (m,1H,6β); 2.05 (s,3H,18); 2.26 (s, 3H,COCH₃); 2.47 (m,1H,6α); 3.58 (d, J=15.0 Hz, 1H, 10β); 3.89 (d, J=6.7 Hz, 1H, 3); 3.92 (d, J=15.0 Hz, 1H, 10α); 3.97 (s,1H,OH-1); 4.27, 4.29 (two doublets, J=8.5 Hz,2H,20); 4.46 (dd, J=6.7, 10.6 Hz,1H,7); 4.77 (d, J=2.1 Hz,1H,OH-14); 4.90 (dd,J=1.7, 9.6 Hz,1H,5); 4.98 (d, J=2.1 Hz,14); 5.82 (d, J=6.7 Hz,1H,2); 7.4–8.1 (m,5H,phenyl); 9.3 (bs,1H, N-OH)

EXAMPLE 17

10-Deacetoxy-13-deoxy-13-acetylimino-baccatin (first method)

To a solution of 10-deacetoxy-13-deoxy-13-imino-baccatin (20 mg, 0.029 mmol) in pyridine (0.5 mL) at 0° C., acetic anhydride (30 μL) was added under stirring. After 1 hour at 0° C. the reaction mixture was poured into cold brine and was extracted with ethyl acetate. The organic layer was washed twice with water, dried over Na₂SO₄ and concentrated under vacuum to yield 19.6 mg of the title product (91% yield). TLC (hexane/ethyl acetate 1:1); Rf=0.7

EXAMPLE 18

10-Deacetoxy-13-deoxy-13-acetylimino-baccatin (second method) and 10-deacetoxy-13-deoxy-13 14 ene-13-acetylamino-baccatin To a solution of 7-O-triethylsilyl-10-deacetoxy-13-deoxy-13-acetylimino-baccatin (23 mg, 0.03mmol) in THF (4 mL) at 0° C., 1M tetrabutylammonium fluoride in THF (7μL) was added. The reaction mixture was stirred at 0° C. for 2 hours; then it was poured into ice-water and extracted with ethyl acetate. The organic layer was separated, washed with brine, with water, dried over Na₂SO₄ and concentrated under vacuum. The residue was purified by preparative chromatography over silica gel (eluant: n-hexane/ethyl acetate 1:1). A mixture of the title products (keto-enolic equilibrium products) was obtained (20 mg, 95% yield) TLC (hexane/ethyl acetate ); Rf=0.12 (I) and Rf=0.7 (Ia).

EXAMPLE 19

7-O-triethylsilyl-10-deacetoxy-11-hydro-12,13 ene-13-deoxy-13-benzoylamino-baccatin To a solution of 7-O-triethylsilyl-10-deacetoxy-13-deoxy-13-imino-baccatin (21 mg, 0.0328 mmol) in anhydrous THF (2 mL) at 0° C., under nitrogen, benzoyl chloride (38μL, 0.327 mmol) and NaBH₃CN (41 mg) were added. After 1 hour at 0° C., the reaction mixture was dissolved in ethyl acetate. The organic solution was poured into ice, the organic phase was washed with brine and dried over Na₂SO₄. The crude product was purified by preparative chromatography over silica gel (eluant n-hexane/ethyl acetate 2:1) to give the title product (16 mg, 65%).

TLC (hexane/ethyl acetate 1:1); Rf 0.41. ¹H-NMR (400 MHz, CDCl₃) 1.16 (s,3H,17); 1.28 (s,3H,16); 1.61 (s,3H, 19); 1.84 (s,3H,18); 1.90 (m,1H,6β); 2.11 (s,3H,CH₃CO); 2.46 (m,1H,6α); 2.64 (d, J=11.7 Hz, 1H, 11); 2.70 (d, J=18.5 Hz,1H,14α); 2.90 (dd, J=13.5,1.2 Hz,1H,10α); 3.00 (dd, J=13.5,11.7 Hz,1H,10β); 3.12 (d, J=18.5 Hz,1H,14β); 3.90 (d, J=5.3 Hz,1H,3); 4.26 (dd, J=7.3,10.5 Hz, 1H, 7); 4.31, 4.35 (two doublets, J=8.5 Hz,2H,20); 4.90 (m,1H,5); 5.50 (dd, J=5.3,1.4 Hz,1H,2); 7.37 (s,1H,PhCONH); 7.4–8.1 (m,10H,two phenyls).

EXAMPLE 20

7-O-triethylsilyl-10-deacetoxy-11-hydro-12.13 ene-13-deoxy-13-isobutanoylamino-baccatin To a solution of 7-O-triethylsilyl-10-deacetoxy-13-deoxy-13-imino-baccatin (30 mg, 0.047 mmol) in anhydrous THF (3 mL) at 0° C., under nitrogen, isobutanoylchloride (40 μL) and NaBH₃CN (60 mg) were added. After 50 minutes at 0° C., the reaction mixture was poured into ice, the organic material was extracted with ethyl acetate and washed with brine and dried over Na₂SO₄. The crude product was purified by preparative chromatography over silica gel (eluant= n-hexane/ethyl acetate 7:3), yielding 24 mg of the title compound (72%).

TLC (n-hexane/ethyl acetate=7:3); Rf=0.51.

EXAMPLE 21

10-Deacetoxy-11-hydro-12,13 ene-13-deoxy-13-isobutanoylamino-baccatin

To a solution of 7-O-triethylsilyl-10-deacetoxy-11-hydro-13-deoxy-12,13-ene-isobutanoyl-baccatin (24 mg, 0.034 mmol) in THF (2 mL), at 0° C. under nitrogen, 50 μL of 1M solution of tetrabutylammonium fluoride in THF was added. After two hours to the reaction mixture ethyl acetate was added, the organic solution was poured into ice, separated, washed with brine, water and dried over Na₂SO₄. The crude product was purified by preparative TLC (eluant: n-hexane/ethyl acetate 1:3), yielding 14 mg (69%) of the title product.

TLC (n-hexane/ethyl acetate 1:4); Rf=0.29. ¹H-NMR (200 MHz, CDCl₃) : 1.06 (s,3H,17); 1.17, 1.21 (two d, J=6.8 Hz,CH(CH₃)₂; 1.24 (s,3H,16); 1.59 (s,3H,19); 1.69 (s,3H, 18); 1.72 (s,1H,OH-1); 1.7–2.0 (m,2H,6β+OH-7); 2.32 (s,3H,COCH₃); 2.3–2.7 (m,4H, (CH₃)₂CHCO+11+6α+14); 2.8–3.0 (m,2H,10α+14β); 3.04 (dd, J=11.2, 13.8 Hz,1H, 10β); 3.73 (d, J=5.3 Hz,1H,3); 4.09 20 (m,1H,7); 4.29, 4.35 (two d, J=8.6 Hz,2H,20); 4.88 (dd, J=2.5, 9.2 Hz,1H,5); 5.53 (dd, J=5.3, 1.0 Hz,1H,2); 6.51 (s,1H,CONH); 7.4–8.1 (m,5H,phenyl).

EXAMPLE 22

10-Deacetoxy-11-hydro-12,13 ene-13-deoxy-13-benzoylamino-baccatin

The removal of the 7-O-triethylsilyl group was performed as described in Example 15.

The title compound was obtained in 75% yield.

TLC (n-hexane/ethyl acetate 1:2); Rf=0.24. ¹H-NMR (200 MHz, CDCl₃) : 1.11 (s,3H,17); 1.25 (s,3H,16); 1.62 (s,3H,19); 1.75 (s,1H,OH-1); 1.81 (s,3H,18); 1.85 (m,1H, 6β); 2.09 (s,3H,CH₃CO-4) 2.4–2.8 (m,3H, 6α+11+14α); 2.91 (dd, J=2.5, 13.8 Hz,1H,10α); 3.0–3.2 (m,2H,10β+14β); 3.84 (d, J=5.2 Hz,1H,3); 4.15 (m,1H,7); 4.27,4.35 (two doublets, J=8.5 Hz,2H,20); 4.89 (dd, J=2.4, 9.2 Hz,1H,5); 5.57 (dd, J=1.0, 5.2 Hz,1H,2); 7.34 (s,1H,CONH); 7.3–8.1 (m,10H, two phenyls).

EXAMPLE 23

7-O-triethylsilyl-10-deacetoxy-13-deoxy-13-phenylacetylimino-baccatin

To a solution of 7-O-triethylsilyl-10-deacetoxy-13-deoxy-13-imino-baccatin (20 mg, 0.031 mmol) and phenylacetic acid (22 mg, 0.16 mmol) in anhydrous THF (2 mL), 1,3-dicyclohexylcarbodiimide (36 mg, 0.174 mmol) and a few crystals of N,N-dimethylaminopyridine were added at room temperature, under nitrogen with stirring. After 40 minutes the reaction mixture was filtered on celite, the filtrate was concentrated and purified on preparative TLC (eluant:n-hexane/ethyl acetate 2.1), yielding 20 mg (84%) of the title compound.

¹H-NMR (200 MHz, CDCl₃) : : 0.5–0.7 (m,6H,Si (CH₂CH₃)₃); 0.9 (m, 9H, Si(CH₂CH₃)₃); 1.15 (s,3H,17); 1.20 (s,3H,16); 1.6 (s,3H,19); 1.9 (m,1H,6β); 2.0 (s, 3H,18); 2.1 (d,1H,14β); ); 2.4 (s,3H,CH₃CO-4); 2.5 (m,1H, 6α); 3.3 (d, 1H,14α); 3.55 (d,1H, 10β) 3.75 (d,2H,CH₂-phenyl); 3.9 (d,1H,10α); 4.05 (m,2H,3+20β); 4.25 (d, 1H,20α); 4.45 (dd,1H,7); 4.90 (m,1H,5); 5.6 (d,1H,2); 7.2–8.1 (m,10H, two phenyls).

EXAMPLE 24

7-O-triethylsilyl-10-deacetoxy-11-hydro-12,13 ene-13-deoxy-13-phenylacetylamino-baccatin To a solution of 7-O-triethylsilyl-10-deacetoxy-13-deoxy-13-phenylacetylimino-baccatin (20 mg, mmol) in anhydrous THF (2 mL), cooled at 0° C., NaBH₃CN (47 mg) and a few crystals of p-toluensulfonic acid were added under nitrogen, with stirring. After 2 hours brine was added to the reaction mixture and the organic material was extracted with ethyl acetate. The organic layer was dried over Na₂SO₄, filtered and concentrated under vacuum. The crude product was purified by preparative TLC (eluant:n-hexane/ethyl acetate 1.5:1), yielding 15 mg (75%) of the title product.

EXAMPLE 25

10-Deacetoxy-11-hydro-12,13 ene-13-deoxy-13-phenylacetylamino-baccatin

The removal of the 7-O-triethylsilyl group was performed as described in Example 15.

The title compound was obtained in 68% yield.

TLC (n-hexane/ethyl acetate 1:2); Rf=0.22. ¹H-NMR (200 MHz, CDCl₃) : 1.07 (s,3H,16); 1.17 (s,3H,17); 1.49 (s,3H,18); 1.57 (s,3H,19); 1.64 (s,1H,OH-1); 1.79 (m,1H, 6β); 2.06 (s,3H,CH₃CO-4) 2.3–2.7 (m,3H, 6α+11+14α); 2.7–2.9 (m,2H,10α+14β); 3.01 (dd, J=11.3,13.7 Hz,1H, 10β); 3.5–3.8 (m,3H,3+PhCH₂CO); 4.04 (dd, J=6.9, 11.1 Hz,1H,7); 4.27,4.32 (two doublets, J=8.5 Hz,2H,20); 4.82 (dd, J=2.5, 9.3 Hz,1H,5); 5.51 (dd, J=1.0, 5.3 Hz,1H,2); 6.49 (s,1H,CONH); 7.2–8.1 (m,10H,two phenyls).

EXAMPLE 26

7-O-triethylsily-10-deacetoxy-11-hydro-12,13 ene-13-deoxy-13-cinnamoylamino-baccatin To a solution of 7-O-triethylsilyl-10-deacetoxy-13-deoxy-13-imino-baccatin (20 mg, 0.031 mmol) in anhydrous THF (2 mL) at 0° C., under nitrogen with stirring, cinnamoyl-chloride (43 mg) and NaBH₃CN (40 mg) were added. After 70 minutes at 0° C., the reaction mixture was poured into ice-water and extracted with ethyl acetate. The organic solution was washed with brine, dried over Na₂SO₄ and concentrated under vacuum. The crude product was purified by preparative chromatography over silica gel (eluant:dichloromethane/ethyl acetate 17:3), yielding 12 mg of the title compound (50%).

EXAMPLE 27

10-Deacetoxy-11-hydro-12,13 ene-13-deoxy-13-cinnamoylamino-baccatin

The removal of the 7-O-triethylsilyl group was performed as described in Example 15.

The title compound was obtained in 73% yield.

TLC (dichloromethane/methanol 19:1); Rf=0.46. ¹H-NMR (200 MHz, CDCl₃) : 1.13 (s,3H,16); 1.24 (s,3H, 17); 1.60 (s,3H,19); 1.78 (s,3H,18); 1.83 (m,1H,6β); 2.29 (s,3H,CH₃CO-4); 2.5–2.8 (m,3H, 6α+11+14α); 2.89 (dd,J= 2.1,13.7 Hz,1H,10α); 3.0–3.3 (m,2H,10β+14β); 3.81 (d,J= 5.1 Hz,1H,3); 4.12 (m, 1H,7); 4.30, 4.36 (two doublets, J=8.6 Hz,2H,20); 4.90 (dd, J=2.3,9.3 Hz,1H,5); 5.56 (d, J=5.1 Hz,1H,2); 6.51 (d,J=15.5 Hz,1H,Ph—CH=CH); 6.74 (s,1H,CONH); 7.69 (d,J=15.5 Hz,1H,Ph—CH=CH); 7.3–8.1 (m,10H, two phenyls).

EXAMPLE 28

7-O-Triethylsilyl-10-deacetoxy-13-deoxy-13-((4S, 5R)-N-benzoyl-2,2-dimethyl-4-phenyl oxazolidin-5-yl)-carbonylimino-baccatin To a solution of 7-0-triethylsilyl-10-deacetoxy-13-deoxy-13-imino-baccatin (50 mg, 0.078 mmol) and (4S,5R)-N-benzoyl-2,2-dimethyl-4-phenyl oxazolidin-5-carboxylic acid (35 mg, 0.107 mmol), in toluene (7 mL), N,N-dicyclohexylcarbodiimide (30 mg, 0.145 mmol) and 4-dimethylaminopyridine (7.5 mg, 0.061 mmol) were added and the reaction mixture was stirred under nitrogen at room temperature for 30 minutes. The reaction mixture was filtered, the solvent evaporated under vacuum and the crude product was purified by preparative chromatography over silica gel (eluant:n-hexane/ethyl acetate 2:1), yielding 57 mg of the title compound (76%).

TLC (n-hexane/ethyl acetate 1:1); Rf 0.58. ¹H-NMR (600 MHz, CDCl₃):0.4–0.7 (m,6H,Si(CH₂ CH₃)₃); 0.81,1.11 (two s,6H,16+17); 0.94 (m,9H,Si(CH₂CH₃)₃);1.58 (s,3H, 19); 1.85 (m,1H,6β); 1.91,1.93,1.93 (three s,9H,18+2 CH₃-5'); 2.35 (d, J=19.0 Hz,1H,14β); 2.41 (s,3H,COCH₃-4); 2.47 (m,1H,6α); 3.23 (d, J=19.0 Hz,1H,14α); 3.52 (d, J=14.5 Hz,1H,10β); 3.88 (d, J=14.5 Hz,1H,10α); 4.02 (d, J=6.6 Hz,1H,3); 4.07 (d,J=8.5 Hz,1H,20β); 4.29 (d,J=8.5 Hz,1H, 20α); 4.48 (dd,J=6.8,10.5 Hz,1H,7); 4.58, 5.22 (two d, J=8.1 Hz, 2H, 2'+3'); 4.87 (d,J=8.5 Hz,1H,5); 5.60 (d, J=6.6 Hz,1H,2); 6.8–8.1 (m,15H,three phenyls).

EXAMPLE 29

10-Deacetoxy-13,14 ene-13-deoxy-13-((4S,5R)-N-benzoyl-2,2-dimethyl-4-phenyl oxazolidin-5-yl)-carbonylamino-baccatin 7-O-Triethylsilyl-10-deacetoxy-13-deoxy-13-((4S,5R)-N-benzoyl-2,2-dimethyl-4-phenyl oxazolidin-5-yl)-carbonylimino-baccatin (20 mg, 0.021 mmol) was dissolved in a mixture of methanol (1 mL), 0.1N HCl (1 mL) and THF (0.5 mL) and stirred for 20 hours at room temperature.

The solvent was evaporated under vacuum, water and ethyl acetate were added, the organic phase was separated and washed with water, dried over Na₂SO₄ and concentrated. The crude product was purified by preparative chromatography over silica gel (eluant:n-hexane/ethyl acetate 3:7), yielding 10 mg of the title compound (50%).

TLC (n-hexane/ethyl acetate 1:5); Rf 0.56. ¹H-NMR (200 MHz, CDCl₃) : 1.12, 1.33 (two s,6H,16+17); 1.65 (s,3H,19); 1.78 (m,2H,6β+OH-1); 1.90, 1.97, 2.00, 2.01 (four s,12H,2 CH₃-5'+18+CH₃CO-4); 2.59 (m,1H, 6α); 3.60 (d,J=15.5 Hz,1H,10β); 3.84 (d, J=15.5 Hz,1H,10α); 3.94 (d,J=7.0 Hz,1H,3); 4.1–4.3 (m,3H,7+20); 4.55, 5.19 (two d, J=6.5 Hz,2H,2'+3'); 4.89 (m, 1H,5); 5.82 (d, J=7.0 Hz,1H,2); 6.35 (s,1H,14); 6.9–8.1 (m,15H,three phenyls); 8.20 (s,1H, NH-13).

EXAMPLE 30

7-O-Triethylsilyl-10-deacetoxy-11-hydro-12,13 ene-13-deoxy -13-((4S,5R)-N-benzoyl-2,2-dimethyl-4-phenyl oxazolidin-5-yl)-carbonylamino-baccatin To a solution of 7-o-triethylsilyl-10-deacetoxy-13-deoxy-13-((4S,5R)-N-benzoyl-2,2-dimethyl-4-phenyl oxazolidin-5-yl)-carbonylimino-baccatin (50 mg,0.052 mmol) in anhydrous THF (6 mL), cooled to 0° C., under nitrogen, sodium cyanoborohydride (73 mg,1.16 mmol) and p-toluensulfonic acid (21 mg,0.12 mmol) were added. The reaction mixture was stirred for 50 minutes, brine and ethyl acetate were added and the organic phase was washed with brine, dried over Na₂SO₄, concentrated under vacuum and filtered through a short pad of silica gel to yield 48 mg of the title compound (96%).

TLC (n-hexane/ethyl acetate 1:1); Rf 0.5. ¹H-NMR (600 MHz, CDCl₃) :0.4–0.7 (m,6H,Si(CH₂CH₃)₃); 0.93 (m,9H, Si(CH₂CH₃)₃); 1.13, 1.23 (two s,6H,16+17); 1.47 (s,1H, OH-1); 1.58 (s,3H,19); 1.83 (s,1H,18); 1.90 (m,1H, 6β); 2.01,2.02 (two s, 6H,2 CH₃-5'); 2.29 (s,3H,COCH₃-4); 2.45 (m,1H,6α); 2.58 (d, J=18.5 Hz,1H,14α); 2.65 (d,J=12.2 Hz,1H,11); 2.87 (d, J=18.5 Hz,1H,14β); 2.90 (d, J=13.7 Hz,1H,10α); 2.98 (dd, J=13.7,12.2 Hz,1H,10β); 3.84 (d, J=5.1 Hz,1H,3); 4.2–4.4 (m,3H, 7+20); 4.55, 5.24 (two d, J=6.8 Hz,2H, 2'+3'); 4.87 (m,1H,5); 5.46 (d, J=5.1 Hz,1H,2); 7.76 (s,1H,NH-13); 6.9–8.1 (m,15H,three phenyls).

EXAMPLE 31

10-Deacetoxy-11-hydro-12,13 ene-13-deoxy-13-((4S,5R)-N-benzoyl-2,2-dimethyl-4-phenyl oxazolidin-5-yl)-carbonylamino-baccatin 7-O-Triethylsilyl-10-deacetoxy-11-hydro-12,13 ene-13-deoxy -13-((4S,5R) -N-benzoyl-2,2-dimethyl-4-phenyl oxazolidin-5-yl)-carbonylamino-baccatin (14 mg,0.014 mmol) was dissolved in anhydrous ethanol (2 mL) containing 2N HCl (100 mL). The reaction mixture was stirred for 2.5 hours at 40° C. The solvent was evaporated under vacuum, brine and ethyl acetate were added, the organic phase was dried over Na₂SO₄ and concentrated under vacuum. The residue was purified by preparative TLC (eluant ethyl acetate/n-hexane 2:1) to yield 8 mg of the title compound (68%).

TLC (n-hexane/ethyl acetate 1:5); Rf 0.54. ¹H-NMR (600 MHz, CDCl₃): 1.13, 1.24 (two s,6H,16+17); 1.53 (s,1H,OH-1); 1.61(s,3H,19); 1.83 (m,4H,18+6β); 1.99,2.02 (two s, 6H,2 CH₃-5'); 2.29 (s,3H,COCH₃-4); 2.56 (m,1H,6α); 2.60 (d, J=18.6 Hz,1H,14α); 2.65 (d,J=11.6 Hz,1H,11); 2.89 (d, J=18.6 Hz,1H,14β); 2.94 (dd, J=13.9,1.7 Hz,1H,10α); 3.10 (dd, J=13.9,11.6 Hz,1H,10β); 3.84 (d, J=5.1 Hz,1H,3); 4.16 (dd,J=7.8,10.7 Hz,1H, 7); 4.30, 4.34 (two d,J=8.5 Hz,2H, 20); 4.54, 5.22 (two d, J=6.6 Hz,2H, 2'+3'); 4.89 (dd,J=9.2, 2.3 Hz,1H,5); 5.54 (dd, J=5.1, 1.1 Hz,1H,2); 7.77 (s,1H, NH-13); 6.9–8.1 (m,15H,three phenyls).

We claim:

1. A taxane derivative of formula I:

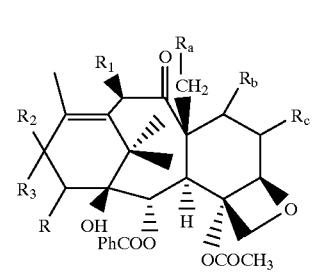

wherein

R represents a hydrogen atom or a hydroxy group, or taken together with R₃, a bond; R$_a$ and R$_c$ are hydrogens and R$_b$ is hydroxy, or R$_a$ and R$_b$ taken together form a bond and $R_c$ is hydrogen, or $R_a$ is hydrogen atom and $R_b$ and $R_c$ taken together form a bond, or $R_b$ is azido or amino group and $R_c$ is hydrogen atom;

$R_1$ represents a hydrogen atom, a hydroxy group or a residue of formula —OCOR', —OR', —OSO$_2$R', —OCONR'R", —OCONHR' or —OCOOR' wherein R' and R" are each independently $C_1$–$C_6$ alkyl, phenyl-$C_2$–$C_6$ alkenyl, or phenyl-$C_2$–$C_6$-alkyl, $C_3$–$C_6$ cycloalkyl, $C_2$–$C_6$ alkynyl or a phenyl group, optionally substituted with one, two or three substituents which may be the same or different and which are selected from a halogen atom and $C_1$–$C_6$ alkyl, $C_1$–$C_6$ alkoxy and —CF$_3$ groups; and either (i) $R_2$ and $R_3$ together represent a group of the formula A—N=, as pure E or pure Z isomers or as a mixture of both E and Z isomers, wherein A represents:
  a hydrogen atom or a hydroxy, methoxy, acetoxy, amino, methylamino or dimethylamino group, or
  a group of the formula Y—NH— wherein Y represents either
    (a) residue of an amino acid, optionally protected at the amino group as a N-benzoyl derivative or as a carbamate, or
    (b) a chain of the formula II:

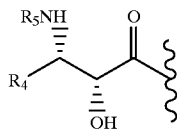

wherein:
  $R_4$ is a $C_1$–$C_6$ alkyl, $C_2$–$C_6$ alkenyl, $C_3$–$C_6$ cycloalkyl group or a phenyl or heteroaryl group, optionally substituted with one, two or three substituents which may be the same or different and which are selected from a halogen atom and $C_1$–$C_6$ alkyl, $C_1$–$C_6$ alkoxy, or —CF$_3$ groups; and
  $R_5$ is —COOR'" or —COR'" or —CONHR'", wherein R'" is $C_1$–$C_6$ alkyl, $C_2$–$C_6$ alkenyl, $C_3$–$C_6$ cycloalkyl, $C_2$–$C_6$ alkynyl or a phenyl group, optionally substituted with one, two or three substituents which may be the same or different and which are selected from a halogen atom and $C_1$–$C_6$ alkyl, $C_1$–$C_6$ alkoxy and —CF$_3$ groups; or
  a group of the formula Y or Y—O— wherein Y is as defined above;
  a group of the formula COR' wherein R' is as defined above; or (ii) R2 represents a group of the formula B—NH— wherein B represents
  a) hydrogen atom,
  b) hydroxy group,
  c) amino group,
  d) a group of the formula Y—(NH)$_n$— wherein Y is as defined above and n is 0 or 1, or
  e) a group of the formula Y—O— wherein Y is as defined above;
  f) a group of the formula COR', wherein R' is as defined above; and $R_3$ represents hydrogen;

and pharmaceutically acceptable salts thereof.

2. A compound according to claim 1 wherein:
  $R_a$ and $R_c$ are hydrogen atoms and $R_b$ is a hydroxy group.
  $R_1$ represents a hydrogen atom, a β-hydroxy group or a residue of formula —OCOR', —OR', —OSO$_2$R', —OCONR'R", —OCONHR' or —OCOOR' wherein R' and R" are each independently $C_1$–$C_4$ alkyl, $C_2$–$C_5$ alkenyl, $C_3$–$C_6$ cycloalkyl, $C_2$–$C_5$ alkynyl or a phenyl group, optionally substituted with one, two or three substituents which may be the same or different and which are selected from a halogen atom and $C_1$–$C_4$ alkyl, $C_1$–$C_4$ alkoxy or —CF$_3$ groups; and either:

(i) $R_2$ and $R_3$ together represent a group of the formula A—N=, as pure E or pure Z isomers or as a mixture of both E and Z isomers, wherein A represents:
  a hydrogen atom, hydroxy, methoxy, acetoxy, amino, methylamino or dimethylamino groups, or
  a group of the formula Y—NH— wherein Y represents either
    (a) residue of an amino acid optionally protected at the amino group as a N-benzoyl derivative or as a carbamate, or
    (b) a chain of the formula II:

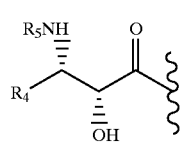

wherein:
  $R_4$ is a $C_1$–$C_4$ alkyl, $C_2$–$C_5$ alkenyl, $C_3$–$C_6$ cycloalkyl group or a phenyl or heteroaryl group, optionally substituted with one, two or three substituents which may be the same or different and which are selected from a halogen atom and $C_1$–$C_4$ alkyl, $C_1$–$C_4$ alkoxy and —CF$_3$ groups;
  $R_5$ is —COOR'" or —COR'" or CONHR'" wherein R'" is $C_1$–$C_4$ alkyl, $C_2$–$C_5$ alkenyl, $C_3$–$C_6$ cycloalkyl, $C_2$–$C_4$ alkynyl or a phenyl group, optionally substituted with one, two or three substituents which may be the same or different and which are selected from a halogen atom and $C_1$–$C_4$ alkyl, $C_1$–$C_4$ alkoxy and —CF$_3$ groups; or
  a group of the formula Y or Y—O— wherein Y is as defined above;

or (ii) $R_2$ represents a group of the formula —NH—B wherein B represents
  a) hydrogen atom,
  b) hydroxy group,
  c) amino group,
  d) a group of the formula Y—(NH)$_n$— wherein Y is as defined above and n is 0 or 1, or
  e) a group of the formula Y—O— wherein Y is as defined above, and $R_3$ represents hydrogen.

3. A compound according to claim 1 wherein Y represents a chain of the formula II as defined in claim 1 or a residue of an amino acid selected from glycine, phenylglycine, serine, 3-phenylserine and β-alanine.

4. A compound according claim 1 wherein $R_1$ is OCOCH$_3$ or a hydrogen atom.

5. A compound according to claim 1 wherein B represents hydrogen or a group of the formula Y— where Y is as defined in claim 1.

6. A compound according to claim 1 which is selected from the group consisting of 13-aza paclitaxel, 13-aza-10-desacetoxy paclitaxel, 13-aza-taxotere, 13-aza-10-deoxy taxotere, 13-aza-10 desacetyl paclitaxel 13-aza-paclitaxel, 13-aza-10-desacetoxy paclitaxel, 13-aza-10-desacetyl paclitaxel, 13-aza-taxotere, 13-aza-10-deoxy-taxotere, 10 deacetoxy-13-deoxy-13-imino paclitaxel, 10,13 dideoxy-13-imino taxotere, 13-deoxy-13-imino paclitaxel, 13-deoxy-13-imino taxotere, 10-deacetoxy-13-deoxy-13,14 ene-13-aza-paclitaxel, 13-deoxy-13,14 ene-13-aza-paclitaxel, 10,13-dideoxy-13,14 ene-13-aza-taxotere, and 13,14 ene-13-aza-taxotere.

7. A process for preparing a taxane derivative of formula I as defined in claim 1, or a pharmaceutically acceptable salt thereof which process comprises: (a) reacting a 7-protected-13-keto-baccatin derivative of formula III

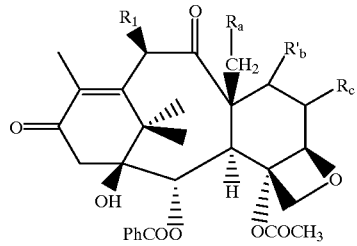

III wherein $R_1$, $R_a$ and $R_c$ are as defined in claim 1 and $R'_b$ is either $R_b$ except for $NH_2$ or OH or a protected amino or hydroxy group, with hydroxylamine, O-methylhydroxylamine, methylhydrazine, N,N-dimethylhydrazine or with ammonia or an ammonium salt and optionally acylating the resulting compound thereby to give a compound of formula IV, IVb, Ivd, IV'd, V or VI:

IV

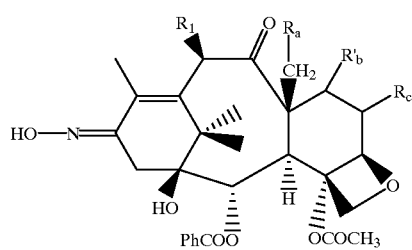

IVb

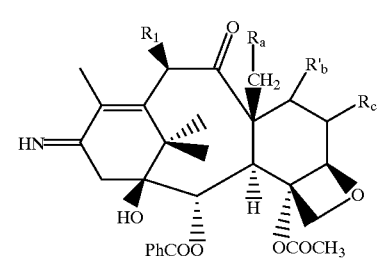

IVd

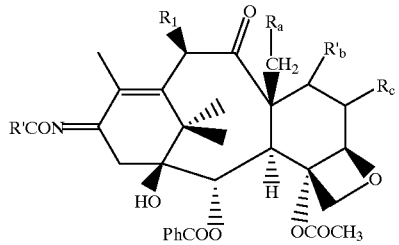

IV'd

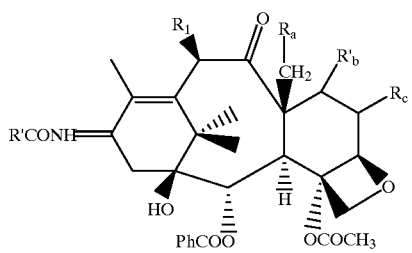

V

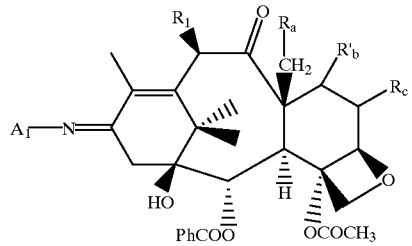

VI

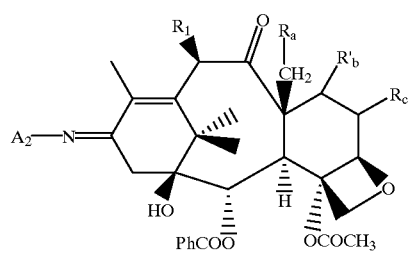

wherein R' is as defined in claim 1, $R_a$, $R'_b$, $R_c$, and $R_1$ are as above defined, $A_1$ represents methoxy or acetoxy and $A_2$ represents a methylamino or dimethylamino group;

(b) optionally reacting the resultant 13-hydrazone of formula VI with anhydrous hydrazine ($H_2N-NH_2$) to give a taxane derivative of formula VII

VII

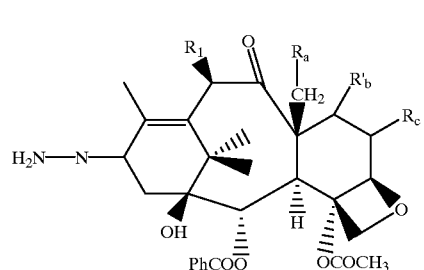

wherein $R_a$, $R'_b$, $R_c$ and $R_1$ as above defined, which is then optionally reduced to a hydrazine derivative of formula VIII:

VIII

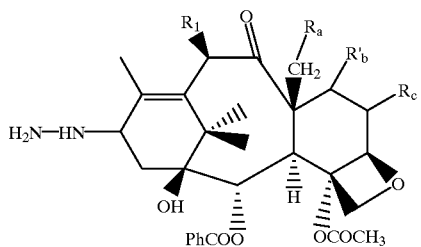

wherein $R_a$, $R'_b$, $R_c$ and $R_1$ are as above defined;

(c) optionally partially reducing the said 13-oxime derivative of formula IV to give the 13-hydroxylamine derivative of formula IVa or the 13-imino derivative of formula IVb as defined above:

IVa

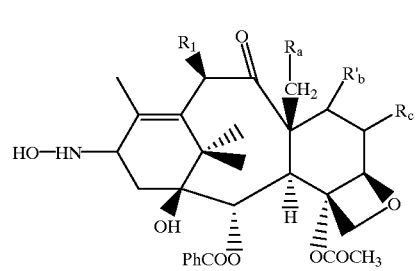

(c') optionally oxidizing a derivative of formula IVb as above defined to give a derivative of formula IVc, IVc

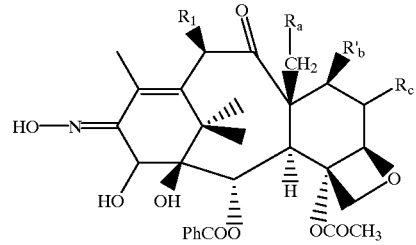

wherein $R_1$, $R_a$, $R'_b$, and $R_c$ are as defined above;

(d) optionally reducing the 13-derivative of formula IV, IVa, IVc, V or VI to give the 13-amino derivative of formula IX:

IX

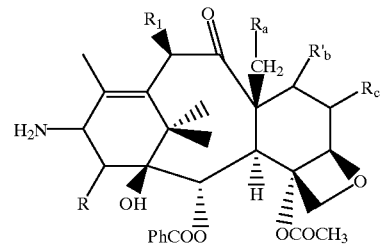

wherein $R_1$, $R_a$, $R'_b$ and $R_c$ are as above defined and R is H or OH;

(e) optionally acylating the C-13 derivative of formula IV, IVa, Ivb VII, VIII or IX with a protected amino acid or with a compound of formula Xa, Xb, Xc or Xd optionally conveniently activated at the carboxy group:

Xa

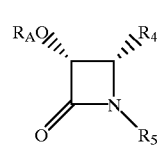

Xb

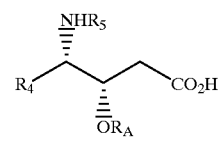

Xc

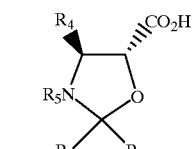

Xd

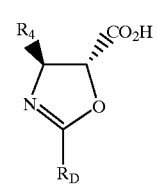

wherein $R_A$ is a hydroxy protecting group and $R_B$ is H or $CH_3$, $R_c$ is $CH_3$ or an optionally substituted phenyl group, $R_D$ is an optionally substituted phenyl group, $R_4$ and $R_5$ are as defined in claim 1, in the presence of a condensing agent to give a protected intermediate of the formula XI:

XI

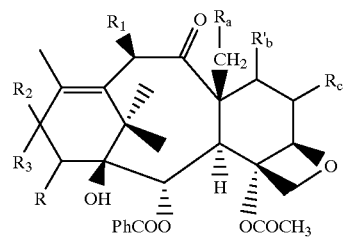

wherein R, $R_a$, $R'_b$, $R_c$ are as above defined, and $R_2$ and $R_3$ are as defined in claim 1 or a protected precursor thereof, (f) deprotecting or reducing when necessary the resultant said compound of the formula IV, IVa, IVb, IVc, IVd, V, VI, VII, VIII, IX or XI to give the said taxane derivative of the formula I; and (g) optionally salifying the said taxane derivative of the formula (I) to give a pharmaceutically acceptable salt thereof.

8. A process according to claim 7, wherein the protected intermediate of formula XI is:

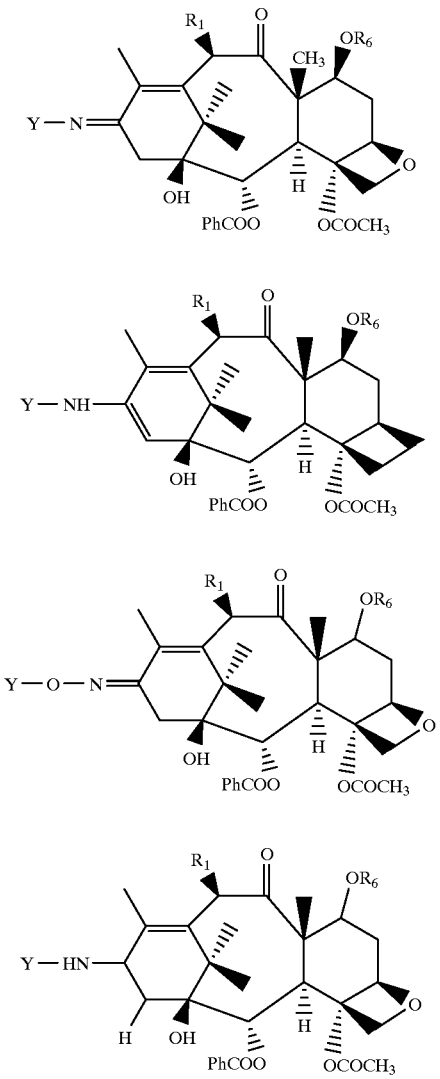

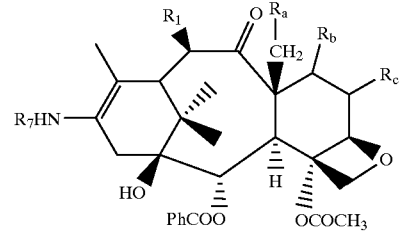

(a) reducing a compound of the formula VIb

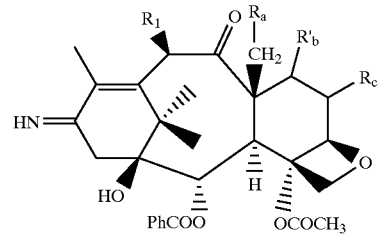

wherein R', $R_1$, $R_a$ and $R_c$ are as defined in claim 1 and $R'_b$ is either $R_b$ as defined in claim 1 except for $NH_2$ or OH or a protected amino or hydroxy group, optionally in the presence of an acylating agent, to give a compound of formula XII

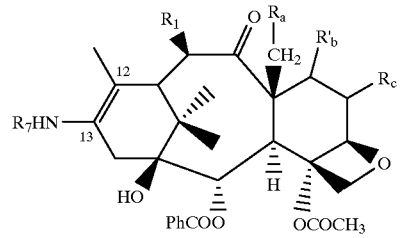

wherein $R_a$, $R'_b$, $R_c$, and $R_1$ are as defined above and $R_7$ is an acyl residue of formula COR' or Y where Y and R' are as defined in claim 1;

(b) deprotecting the compound of formula XII to give said compound of the formula Ia; and (c) optionally salifying the thus obtained compound of formula Ia to give a pharmaceutically acceptable salt thereof.

12. A compound according to claim 10 which is selected from the group consisting of 10-deacetoxy-11 hydro-$\Delta^{12,13}$-13-deoxy-13-aza paclitaxel, 10-deacetoxy-hydro-$\Delta^{12,13}$-13-deoxy-13-aza taxotere, 11-hydro-$\Delta^{12,13}$-deoxy-13-aza paclitaxel, and 11-hydro-$\Delta^{12,13}$-13-deoxy-13-aza taxotere.

13. A pharmaceutical composition which comprises a compound of the formula I as defined in claim 1 or a pharmaceutically acceptable salt thereof together with a pharmaceutically acceptable diluent or carrier.

wherein $R_6$ is a hydroxy protecting group.

9. A compound of the formula IV, IVa, IVb, IVc, IVd, V, VI, VII, VIII, IX or XI as defined in claim 7.

10. A compound of formula Ia

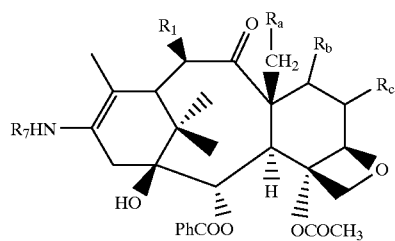

wherein $R_1$ $R_a$, $R_b$ and $R_c$ are as defined in claim 1 and $R_7$ represents a hydrogen atom or an acyl residue of formula COR' or Y wherein Y and R' are defined in claim 1 and pharmaceutically acceptable salts thereof.

11. A process for preparing a compound of formula Ia or a pharmaceutically acceptable salt thereof, which process comprises:

14. A compound which is
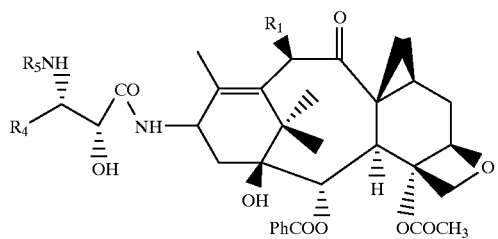
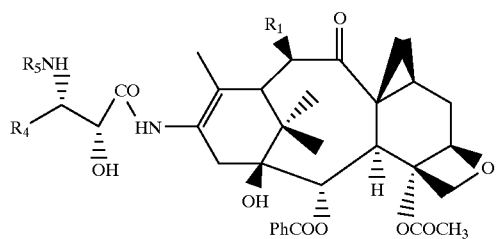
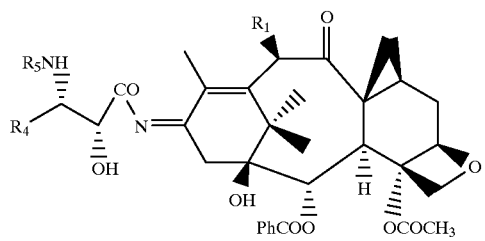
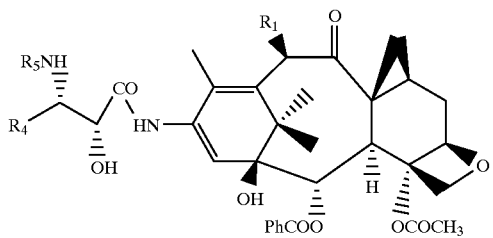
wherein $R_1$, $R_4$ and $R_5$ are as defined in claim 1.
15. A compound which is
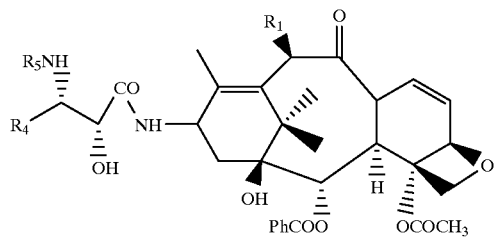
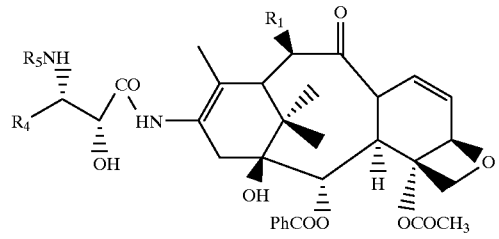
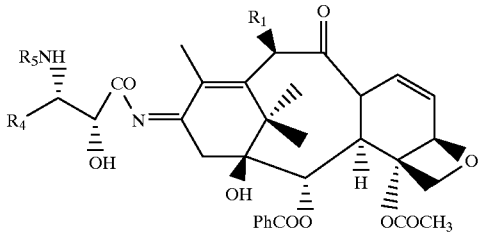
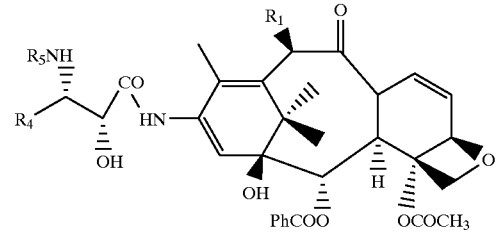
wherein $R_1$, $R_4$ and $R_5$ are as defined in claim 1.
16. A compound which is
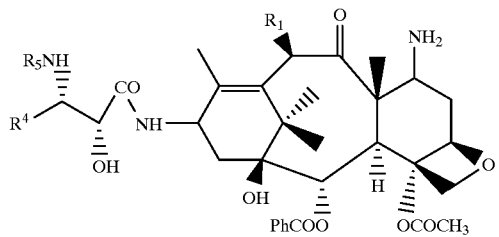
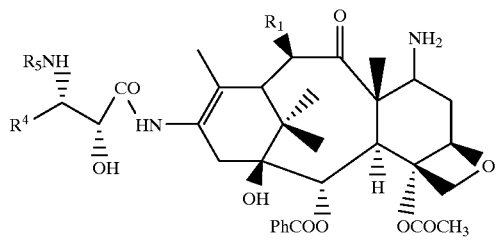

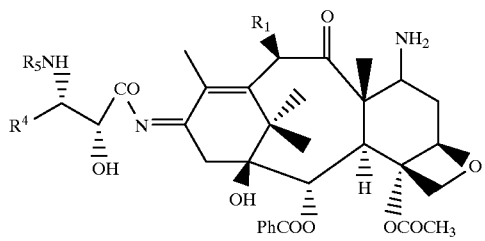

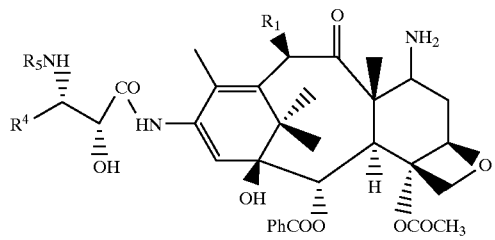

wherein $R_1$, $R_4$ and $R_5$ are as defined in claim 1.

17. A compound which is

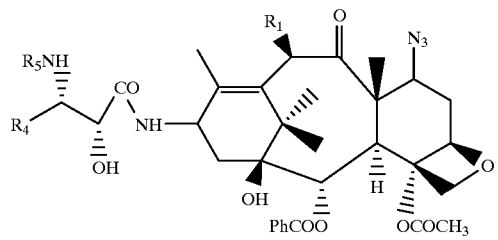

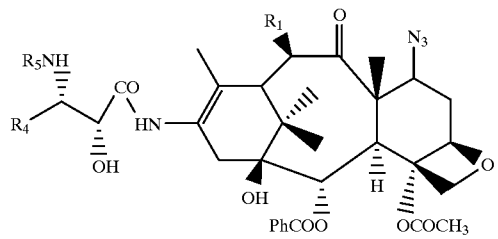

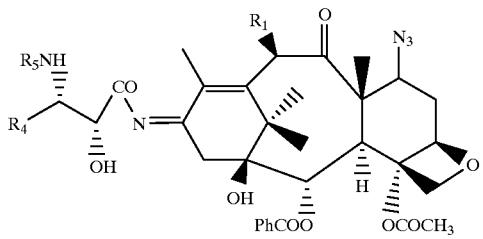

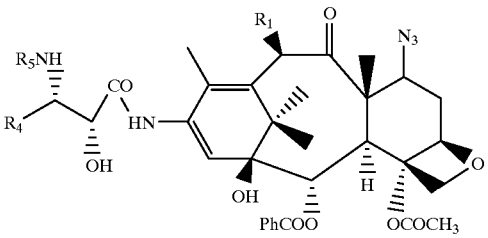

wherein $R_1$, $R_4$ and $R_5$ are as defined in claim 1.

18. A pharmaceutical composition which comprises the compound of claim 9 or a pharmaceutically acceptable salt thereof together with a pharmaceutically acceptable diluent or carrier.

19. A pharmaceutical composition which comprises the compound of claim 10 or a pharmaceutically acceptable salt thereof together with a pharmaceutically acceptable diluent or carrier.

20. A method of treating a tumor in a human or animal in need thereof, comprising administering to said human or animal an effective amount of the taxon of claim 1.

21. A method of treating a tumor in a human or animal in need thereof, comprising administering to said human or animal an effective amount of the compound of claim 9.

22. A method of treating a tumor in a human or animal in need thereof, comprising administering to said human or animal an effective amount of the compound of claim 10.

* * * * *